(12) United States Patent
Chen et al.

(10) Patent No.: US 6,657,351 B2
(45) Date of Patent: Dec. 2, 2003

(54) CONTACTLESS ENERGY TRANSFER APPARATUS

(75) Inventors: James C. Chen, Bellevue, WA (US); Darrin Huston, Enumclaw, WA (US); Brian D. Wilkerson, Issaquah, WA (US)

(73) Assignee: Light Sciences Corporation, Snoqualmie, WA (US)

( * ) Notice: Subject to any disclaimer, the term of this patent is extended or adjusted under 35 U.S.C. 154(b) by 0 days.

(21) Appl. No.: 09/910,364

(22) Filed: Jul. 20, 2001

(65) Prior Publication Data

US 2001/0045785 A1 Nov. 29, 2001

Related U.S. Application Data

(62) Division of application No. 09/547,700, filed on Apr. 11, 2000, which is a continuation-in-part of application No. 09/325,022, filed on Jun. 3, 1999, now Pat. No. 6,092,531, which is a division of application No. 09/021,693, filed on Feb. 10, 1998, now Pat. No. 5,945,762.

(51) Int. Cl.[7] .............................................. H02K 33/00
(52) U.S. Cl. ..................... 310/171; 310/40 R; 310/50; 310/104; 310/112; 290/1 R
(58) Field of Search .................. 310/166, 96, 103–104, 310/112, 171, 40 R, 46, 50, 75 R, 92; 290/1 R; 336/110, 130

(56) References Cited

U.S. PATENT DOCUMENTS

| | | | |
|---|---|---|---|
| 2,481,196 A | 9/1949 | Bulliet | 310/171 |
| 3,668,448 A | 6/1972 | Hayasaka | 310/166 |
| 3,672,352 A | 6/1972 | Summers | 128/2 R |
| 3,817,237 A * | 6/1974 | Bolduc | 128/843 |
| 3,836,289 A | 9/1974 | Wolford et al. | 417/415 |
| 3,942,535 A | 3/1976 | Schulman | 128/419 PS |
| 3,967,146 A | 6/1976 | Howard | 310/80 |

(List continued on next page.)

OTHER PUBLICATIONS

Hilton, Edgar F., et al. "Magnetic Suspension Controls for a New Continuous Flow Ventricular Assist Device." ASAIO Journal, 1977, 43:M598–M603.

Kono, Satoshi, et al. "In Vivo and In Vitro Evaluation of the Pulsatile Mode of a Magnetically Suspended Centrifugal Pump." ASAIO Journa., 1977, 43:M580–M584.

Matsushita Electronic Components Website. Mobile communications equipment. Online. Aug. 17, 1999. Available http://www.maco.panasonic.co.jp/htm–bin/maco/corpo/a5a_3.html. 1 pg.

(List continued on next page.)

Primary Examiner—Burton Mullins
(74) Attorney, Agent, or Firm—Ronald M. Anderson

(57) ABSTRACT

A flux generator base unit electromagnetically coupled with a receiving unit to transfer energy into the receiving unit. The base unit includes one or more permanent magnets that produce a magnetic flux, which passes through a receiver coil in the receiving unit. The receiver coil is either disposed in a separate housing that is electrically connected with a portable device, or integrated into the housing of the portable device. Either the permanent magnets or a flux shunt is moved in the base unit to produce the varying magnetic flux that is coupled to the receiver coil. As a result of the varying magnetic field experienced by the receiver coil, an electric current is induced in the receiver coil, which is conditioned (e.g., rectified, filtered, and regulated) by a conditioning circuit to charge a battery or energize electronics contained in the portable device. Various embodiments of both the base unit and receiving unit are disclosed, including "universal" base units suitable for operation with different size receiving units.

5 Claims, 17 Drawing Sheets

U.S. PATENT DOCUMENTS

| | | | |
|---|---|---|---|
| 4,005,346 A | 1/1977 | Hsia | 318/128 |
| 4,038,572 A | 7/1977 | Hanagan | 310/46 |
| 4,038,625 A | 7/1977 | Tompkins et al. | 336/83 |
| 4,082,936 A | 4/1978 | Aoki et al. | 219/10.41 |
| 4,163,164 A | 7/1979 | Pieters | 310/103 |
| 4,185,617 A * | 1/1980 | Hutchins | 600/16 |
| 4,338,951 A | 7/1982 | Saliga | 128/695 |
| 4,340,038 A * | 7/1982 | McKean | 600/12 |
| 4,392,071 A | 7/1983 | Gauthier | 310/113 |
| 4,432,363 A | 2/1984 | Kakegawa | 128/419 PS |
| 4,443,776 A | 4/1984 | Cunningham | 335/302 |
| 4,461,302 A | 7/1984 | Phillipps et al. | 128/630 |
| 4,507,048 A | 3/1985 | Belenger et al. | 415/90 |
| 4,511,777 A | 4/1985 | Gérard | 219/10.51 |
| 4,564,778 A | 1/1986 | Yoshida | 310/177 |
| 4,665,896 A | 5/1987 | LaForge et al. | 128/1 D |
| 4,679,560 A | 7/1987 | Galbraith | 128/419 R |
| 4,736,752 A | 4/1988 | Munck et al. | 128/798 |
| 4,741,339 A | 5/1988 | Harrison et al. | 128/419 PS |
| 4,761,527 A | 8/1988 | Mohr | 219/10.41 |
| 4,798,926 A | 1/1989 | Sakai | 219/10.43 |
| 4,831,299 A | 5/1989 | Hayasaka | 310/166 |
| 4,927,337 A | 5/1990 | Lustwerk | 417/420 |
| 5,109,843 A | 5/1992 | Melvin et al. | 128/419 R |
| 5,112,200 A | 5/1992 | Isaacson et al. | 417/356 |
| 5,146,123 A | 9/1992 | Yarr | 310/15 |
| 5,274,207 A | 12/1993 | Griffith | 219/10.491 |
| 5,314,457 A | 5/1994 | Jeutter et al. | 607/116 |
| 5,350,413 A | 9/1994 | Miller | 607/61 |
| 5,550,452 A | 8/1996 | Shirai et al. | 320/107 |
| 5,569,156 A | 10/1996 | Mussivand | 600/16 |
| 5,690,851 A | 11/1997 | Yoshioka et al. | 219/635 |
| 5,710,502 A | 1/1998 | Poumey | 320/107 |
| 5,945,762 A | 8/1999 | Chen et al. | 310/171 |
| 5,959,433 A | 9/1999 | Rohde | 320/108 |
| 6,011,245 A | 1/2000 | Bell | 219/631 |

OTHER PUBLICATIONS

Panasonic Design and Specifications printout. Contactless Charger. Undated. 1 pg.

Pansonic® Industrial Company Website. OEM Communications Components (Power Supplies). Online. Aug. 17, 1999. Available http://www.panasonic.com/industrial_oem/communicat . . . /communications_power_supplies.ht. 1 pg.

Paulus, Joseph A., Richardson, Jon S., Tucker, Robert D., and Park, Joon B. "Evaluation of Inductively Heated Ferromagnetic Alloy Implants for Therapeutic Interstitial Hyperthermia." *IEEE Transactions on Biomedical Engineering*, vol. 43, No. 4, Apr. 1996, pp. 406–413.

TDK USA Corporation Website. Application Notes. Online. Aug. 17, 1999. Available http://power.tdk.com/dcdc/applicat1.htm. 1 pg.

TDK. DC–DC Converter Unit brochure. Contactless Charger P/N IBC–131. No Date. 6 pp.

Xu, Longya, et al. "Analysis of a New PM Motor Design for a Rotary Dynamic Blood Pump." ASAIO Journal, 1997, 43:M559–M564.

Yamane, Takashi, et al. "Fluid Dynamic Characteristics of Monopivot Magnetic Suspension Blood Pumps." ASAIO Journal, 1997, 43:M635–M638.

* cited by examiner

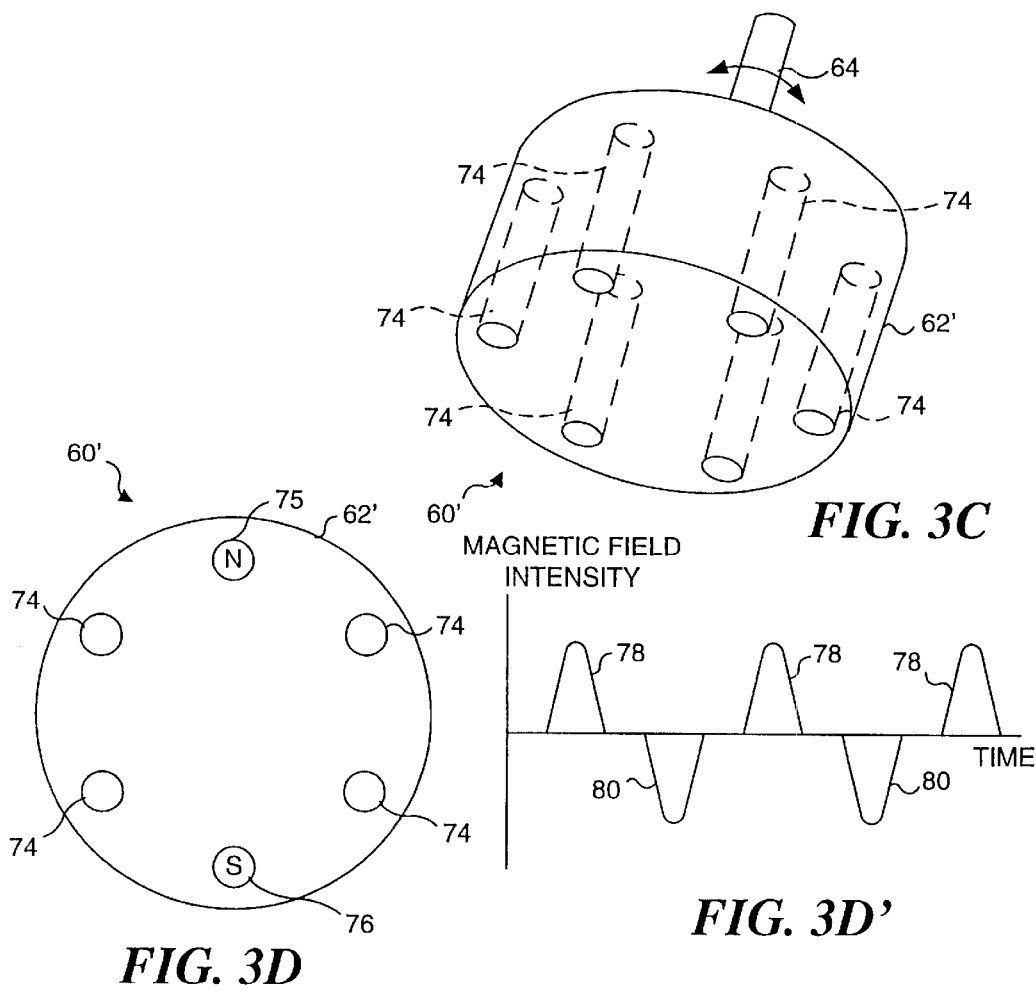
*FIG. 3C*
*FIG. 3D*
*FIG. 3D'*
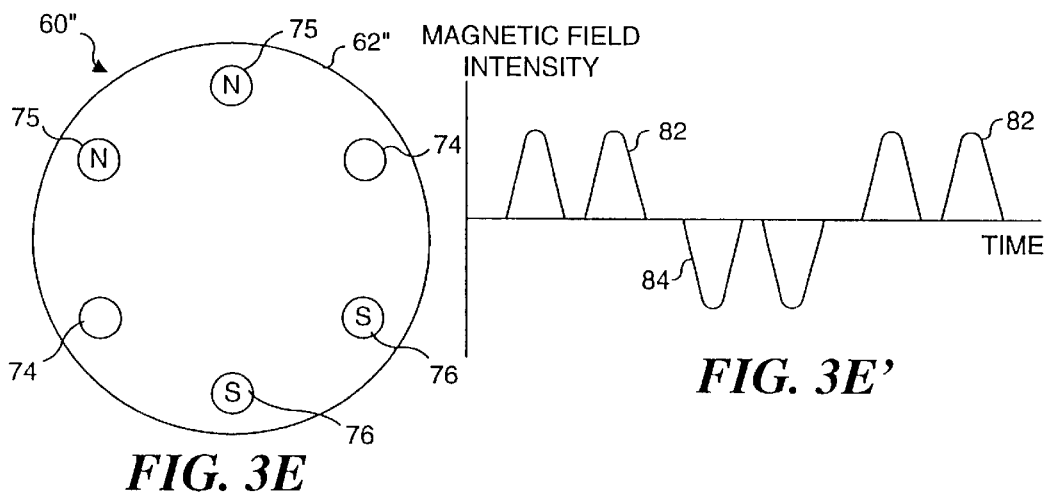
*FIG. 3E*
*FIG. 3E'*

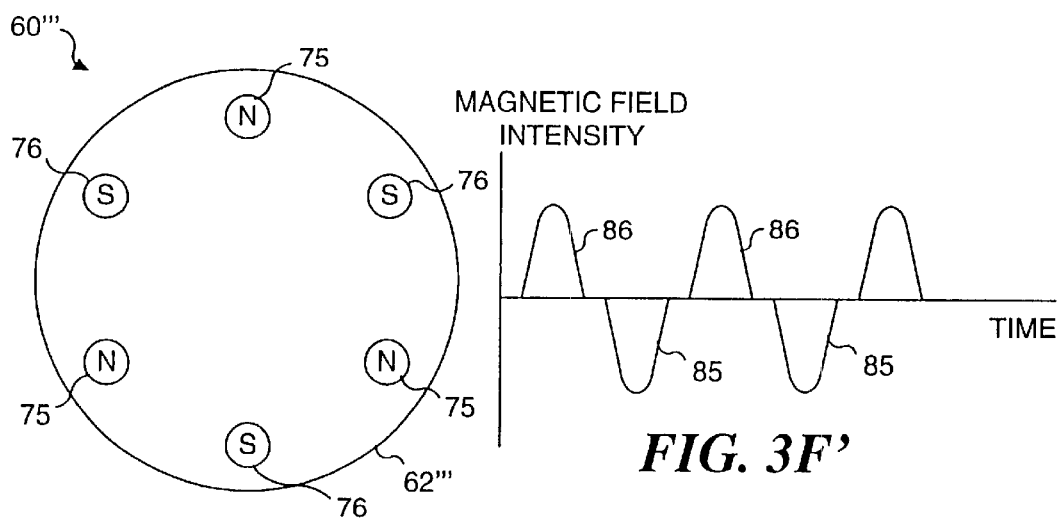
FIG. 3F
FIG. 3F'
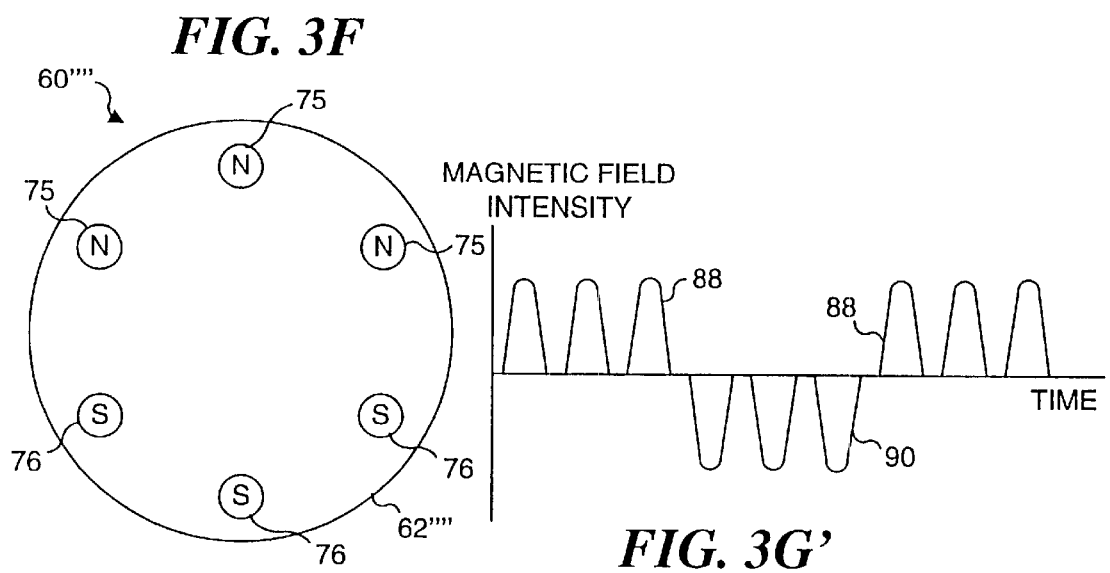
FIG. 3G
FIG. 3G'
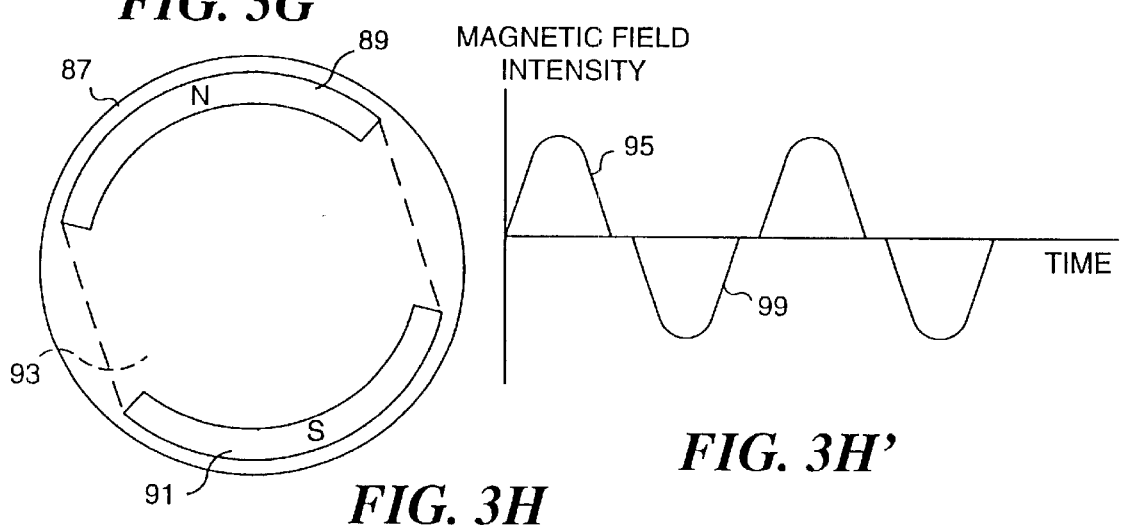
FIG. 3H
FIG. 3H'

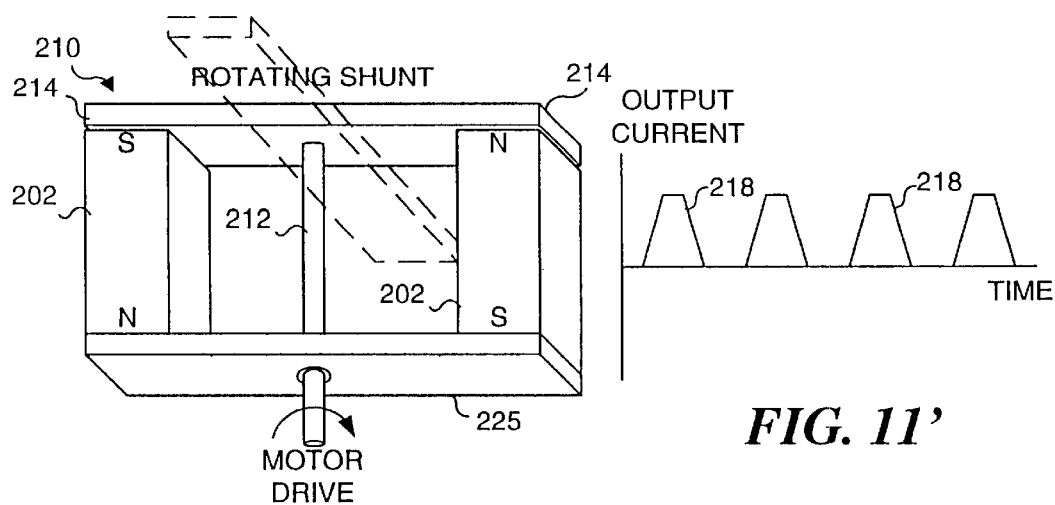
FIG. 11
FIG. 11'
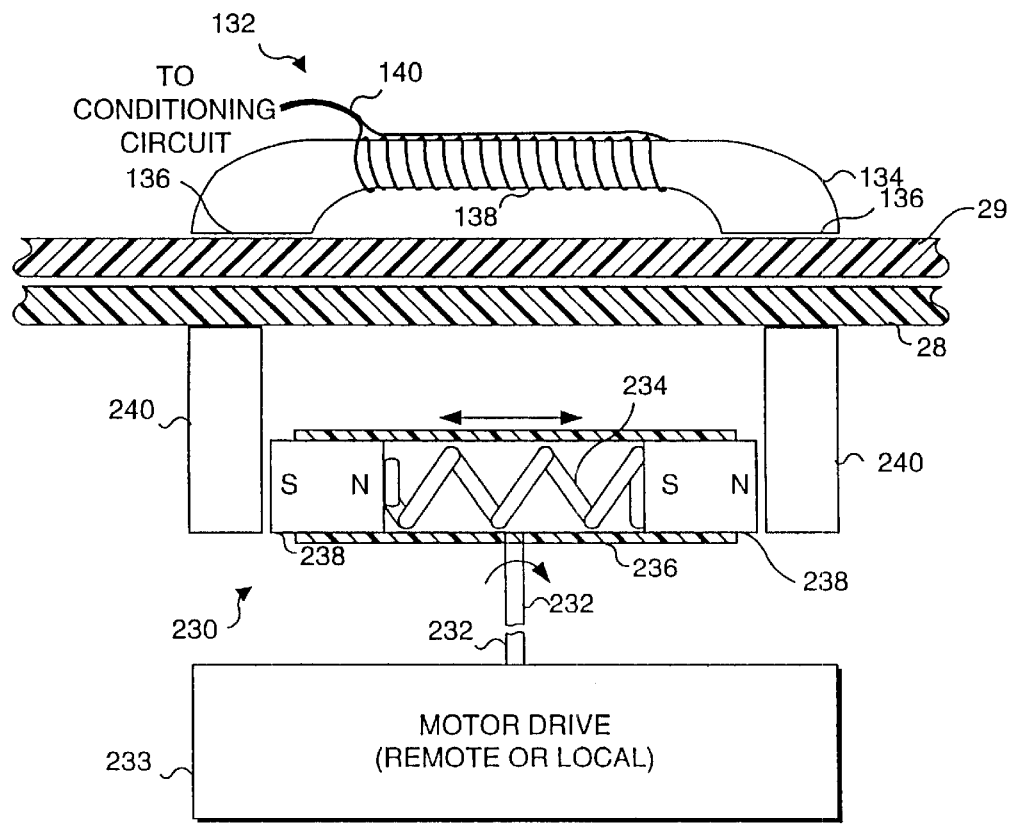
FIG. 12

CONTACTLESS ENERGY TRANSFER APPARATUS

RELATED APPLICATIONS

This application is a divisional application, based on prior copending application Ser. No. 09/547,700, filed Apr. 11, 2000, continuation-in-part of application Ser. No. 09/325,022, filed Jun. 3, 1999, now U.S. Pat. No. 6,092,531 which is a divisional application of Ser. No. 09/021,693, filed on Feb. 10, 1998, now U.S. Pat No. 5,945,762 the benefit of the filing dates of which is hereby claimed under 35 U.S.C. §120.

FIELD OF THE INVENTION

The present invention generally pertains to contactless transfer of electrical energy, and more specifically, to the contactless transfer of electromagnetic energy between disparate devices by moving a magnet in one of the devices to vary a magnetic flux experienced by the other device.

BACKGROUND OF THE INVENTION

Many of today's portable consumer devices, including palm-sized computers, games, flashlights, shavers, radios, CD players, phones, power tools, small appliances, tooth brushes, etc., are powered by rechargeable batteries. The batteries in these devices, which are typically of the nickel-cadmium, lead-acid, nickel-metal-hydride, or lithium-ion type, must be recharged periodically to enable the continued use of the devices.

There are several methods used in the prior art to recharge such batteries. For example, many manufacturers produce rechargeable batteries corresponding to conventional AAA, AA, A, B, C, and D sizes, which are typically recharged using a charger station that is adapted to charge a certain size battery or a plurality of different size batteries. In addition, many power tool manufacturers produce lines of portable tools energized by batteries that are not of the standard sizes listed above, but which often share a common form factor and voltage rating. These batteries are typically recharged by removing the battery from the tool and charging it in a specially-adapted charger specific to that manufacturer's line of tools and specifically designed to recharge batteries of that voltage. In order to recharge both conventional-size batteries and the more specialized portable power tool batteries, it is generally necessary to remove the batteries from the portable device and attach them to their respective chargers, and after they are recharged, the batteries must be reinstalled in the portable device. This task is unduly burdensome and time-consuming for the user.

In order to avoid the burden associated with the foregoing task, some portable consumer devices include a charge-conditioning circuit (either internally or externally) that can be used with a conventional power source, such as a wall outlet, to provide a conditioned direct current (DC) at a voltage suitable for recharging a battery contained in the device. For example, it is common for electric shavers to include a charge-conditioning circuit that enables a nickel-cadmium (or other type) battery retained in the shaver to be recharged by plugging the shaver into a line voltage outlet. Similarly, some flashlights have an integrated connector that allows them to be recharged by simply plugging them into a wall outlet. In addition, certain devices such as portable hand vacuum cleaners use a "base" charger unit for both storing the device between uses and recharging the battery. When the portable device is stored in the base unit, exposed terminals on the device are connected through contacts on the base unit to a power supply energized with line current, thereby providing a conditioned DC current to charge the battery within the portable device.

In all of the foregoing examples, as is true of the majority of devices that use rechargeable batteries, some sort of interface comprising an electrical connection (i.e., contact) is used to provide an appropriate DC voltage for recharging the batteries. However, the use of contacts to connect a battery to a recharging current is undesirable, as they are susceptible to breakage, corrosion, and may present a potential safety problem if used improperly or inadvertently shorted. The shape and configuration of these contacts are also generally unique to individual devices, or a manufacturer's product line, making it impractical to provide a "universal" charging interface that includes contacts.

Recognizing the problems with recharging batteries with current supplied through electrical contacts, several manufacturers now offer "contactless" battery-charging devices. These charging devices are generally of two types—inductive charging systems, and infrared charging systems. Inductive charging systems include an electromagnetic or radio frequency coil that generates an electromagnetic field, which is coupled to a receiver coil within the device that includes a battery requiring recharging. For use in recharging a battery in a handheld powered toothbrush, a relatively high-frequency current is supplied to the transmitter coil in a base for the handheld toothbrush, thereby generating a varying magnetic field at a corresponding frequency. This magnetic field is inductively coupled to a receiver coil in the toothbrush housing to generate a battery charging current. Another example of such a system is the IBC-131 contactless inductive charging system by TDK Corporation, which switches a nominal 141 volt, 20 mA (max) input current to a transmitter coil at 125 kHz to produce a 5 volt DC output at 130 mA in a receiver coil.

A different contactless system for charging batteries is an infrared charging system employing a light source as a transmitter and a photocell as a receiver. Energy is transferred from the source to the receiving photocell via light rather than through a magnetic field.

Both inductive and infrared charging systems have drawbacks. Notably, each system is characterized by relatively high-energy losses, resulting in low efficiencies and the generation of excessive heat, which may pose an undesirable safety hazard. Additionally, the transmitter and receiver of an inductive charging system generally must be placed in close proximity to one another. In the above-referenced TDK system, the maximum gap between the receiver and transmitter is 4 mm. Furthermore, in an infrared system, the light source and/or photocell are typically protected by a translucent material, such as a clear plastic. Such protection is typically required if an infrared charging system is used in a portable device, and may potentially affect the aesthetics, functionality, and/or durability of the device.

It would therefore be desirable to provide a contactless energy transfer apparatus suitable for use with portable consumer devices that allows a greater spacing between the transmitter and receiver elements, and provides improved efficiency over the prior art. Furthermore, it is preferable that such an apparatus provide a contactless "universal" interface for use with a variety of different types and/or different sizes of devices made by various manufacturers.

SUMMARY OF THE INVENTION

In accord with the present invention, an energy transfer apparatus is defined that is adapted for magnetically exciting a receiver coil that includes a core of a magnetically permeable material, by causing an electrical current to flow in the receiver coil. The energy transfer apparatus includes a magnetic field generator that is enclosed in a housing and includes at least one permanent magnet. The housing is adapted to be disposed proximate another housing in which the receiver coil is disposed. A prime mover is drivingly coupled to the magnetic field generator to cause an element of the magnetic field generator to move relative to its housing. Movement of the element produces a varying magnetic field that couples with the core of the receiver coil and induces an electrical current to flow in the receiver coil.

The prime mover of the energy transfer apparatus preferably comprises an electric motor, but can include other types of devices capable of moving the element. For example, a hand crank can be employed for moving the element. In one form of the invention, the prime mover is disposed within the housing in which the magnetic field generator is enclosed. Alternatively, the prime mover is disposed remote from the magnetic field generator and is coupled to the magnetic field generator through a drive shaft.

In several embodiments of the invention, the prime mover moves the permanent magnet relative to the receiver coil. Movement of the permanent magnet varies a magnetic flux along a path that includes the receiver coil. Increasing a speed at which the permanent magnet is moved increases a magnitude of the electrical current induced in the receiver coil.

In one embodiment, the permanent magnet is reciprocated back and forth relative to the receiver coil. The reciprocating movement of the permanent magnet varies a magnetic flux along a path that includes the receiver coil.

A flux linkage bar formed of a magnetically permeable material is preferably disposed adjacent a magnetic pole of the permanent magnet. The flux linkage bar enhances the coupling of magnetic flux from a pole of the permanent magnet into a path that includes the receiver coil.

In several embodiments, the magnetic field generator preferably comprises a plurality of permanent magnets. An adjustment member is included to selectively vary a maximum magnetic flux produced by the magnetic field generator for coupling with the receiver coil. A speed control is used as the adjustment member in one embodiment.

In another embodiment, the permanent magnets include a "driven" permanent magnet that is moved by the prime mover, and a "follower" permanent magnet that is magnetically coupled to the driven permanent magnet and is moved by its motion.

In yet another embodiment, the permanent magnets are fixed relative to the housing, and the moving element comprises a flux shunt that is moved by the prime mover to intermittently pass adjacent to pole faces of the plurality of permanent magnets so as to intermittently provide a magnetic flux linkage path between the pole faces that effectively shunts the magnetic flux. When the magnetic flux is thus shunted, substantially much less magnetic flux couples to the receiver coil. The shunting of the magnetic flux through the moving element effectively periodically "shuts off" the magnetic field produced by the permanent magnets that would otherwise be experienced by the receiving coil, producing the varying magnetic field.

A further technique for adjusting the maximum magnetic field employs a plurality of turns of a conductor that are wound around each the plurality of permanent magnets. The plurality of turns of the conductor are connected to a source of an electrical current, producing a magnetic field that either opposes or aids the magnetic field produced by the permanent magnets, thereby varying the maximum magnetic field experienced by the receiver coil.

In yet another embodiment, the permanent magnets are radially movable relative to an axis of a drive shaft that is rotatably driven by the prime mover. The permanent magnets are attracted to each other when the shaft is at rest, but an actuator moves the permanent magnets away from each other to improve the coupling of the magnetic flux with the receiver coil when the shaft is rotating. The disposition of the permanent magnets adjacent to each other when the shaft begins to rotate reduces the startup torque required to rotate the shaft. Furthermore, by controlling the radial disposition of the permanent magnets, a magnitude of the electrical current induced in the receiver coil is selectively controlled.

According to further aspects of the invention, a contactless battery charger/energy transfer apparatus is defined that use the foregoing energy transfer scheme in combination with a conditioning circuit to recharge a rechargeable storage battery disposed in a portable device. Additionally, the energy can be supplied to electronic components in the portable device. The contactless battery charger/energy transfer apparatus typically includes a flux generator base unit, and a receiver unit. The flux generator is housed in the flux generator base unit, which in several embodiments preferably includes a "universal" mounting provision that enables the base unit to be used with receiver units of different sizes. The receiver unit comprises a receiver coil disposed in a housing adapted to mate with the base unit, and a conditioning circuit that conditions the current generated by the energy inductively coupled into the receiver coil to control the charging of a battery (or batteries) and/or provide a conditioned current to the electronic components in the portable device. The receiver coil housing may be integral to the portable device in which the receiver coil is disposed, or it may be a separate component that is suitable for attachment to a variety of different devices.

In one preferred embodiment, the flux generator base unit and receiver units are shaped in the form of tablets. The contactless battery charger/energy transfer apparatus embodiments additionally provide a sensor and an indicator for detecting and indicating when the receiver unit is mated and properly aligned with the flux generator base unit. The sensor signal controls the operation of the motor. The conditioning circuit also includes a detection circuit for determining when a battery is fully charged, and controls the charge current supplied to the battery as a function of its charge state. Also included in the flux generator base unit is a detection circuit for determining when the battery is charged, so that the motor is then turned de-energized.

According to another aspect of the invention, a wireless communication channel is effected between the receiver unit and the flux generator base unit by pulsing a load applied to the output of the conditioning circuit, thereby producing a corresponding pulse change in the current supplied to the electric motor. The pulsing current drawn by the electric motor is detected to recover the data transmitted from the receiver unit.

Another aspect of the present invention is directed to a method for charging a battery via a varying magnetic field that is inductively coupled to transfer energy to a receiver coil. The steps of this method are generally consistent with the functions provided by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 3A:
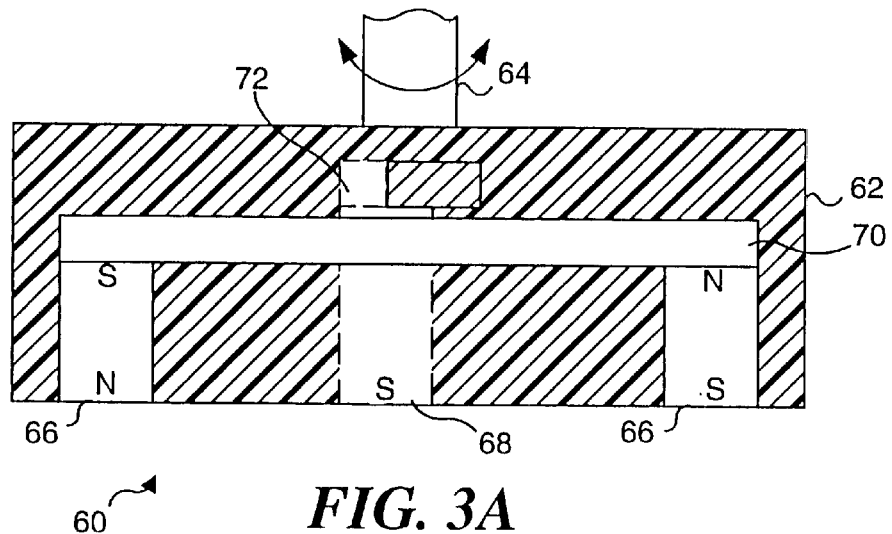
Figure 3B:
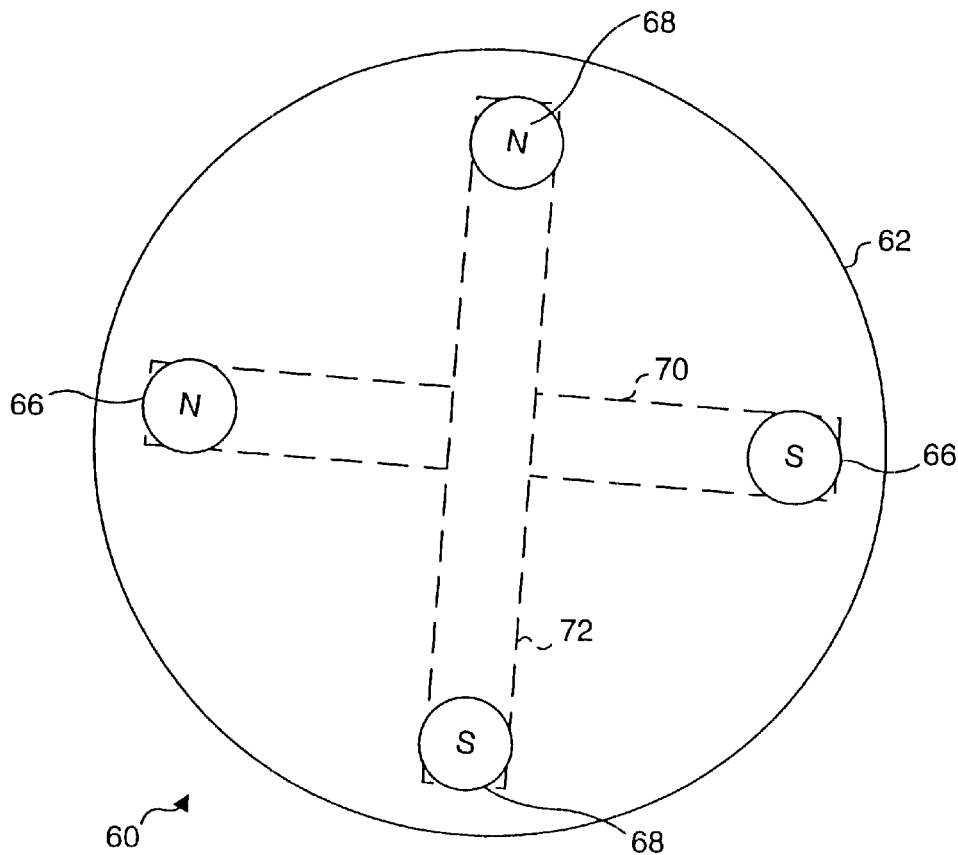
Figure 4A:
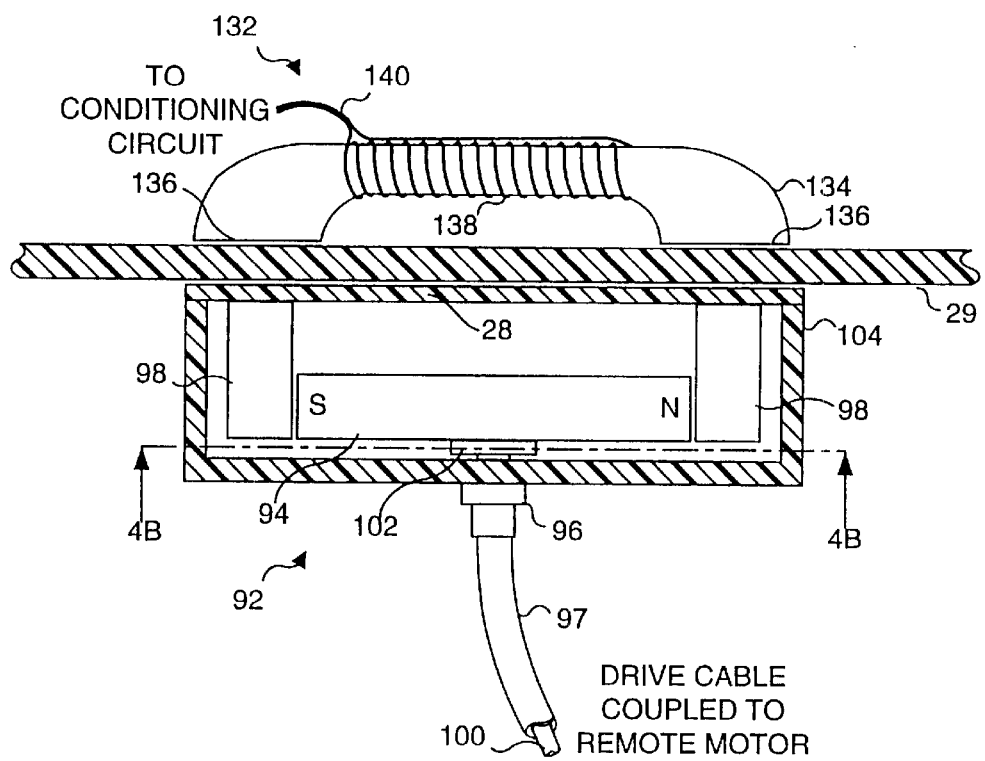
Figure 4B:
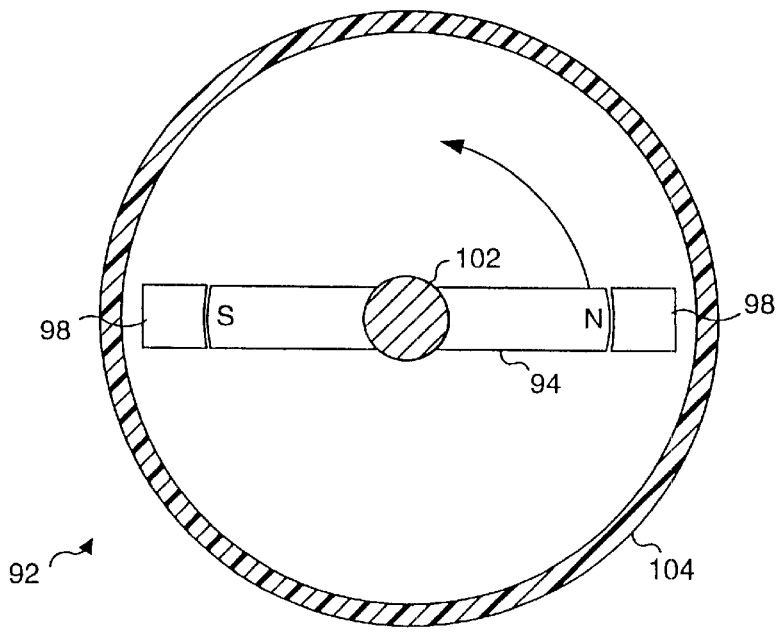
Figure 5:
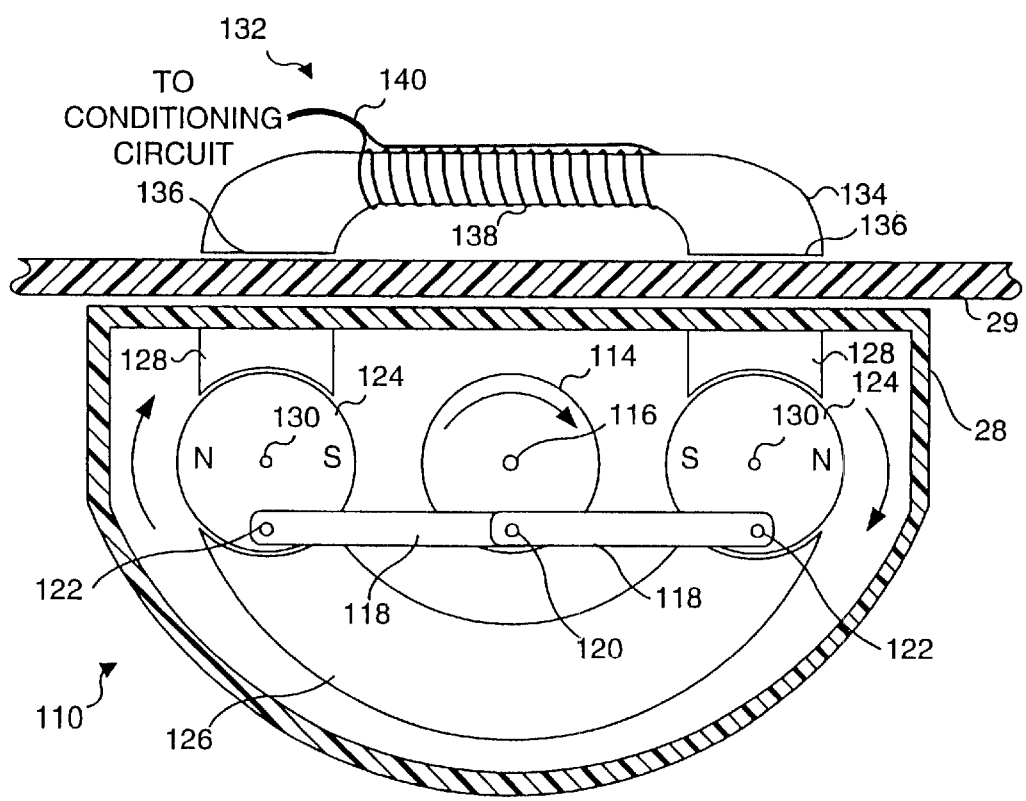
Figure 6A:
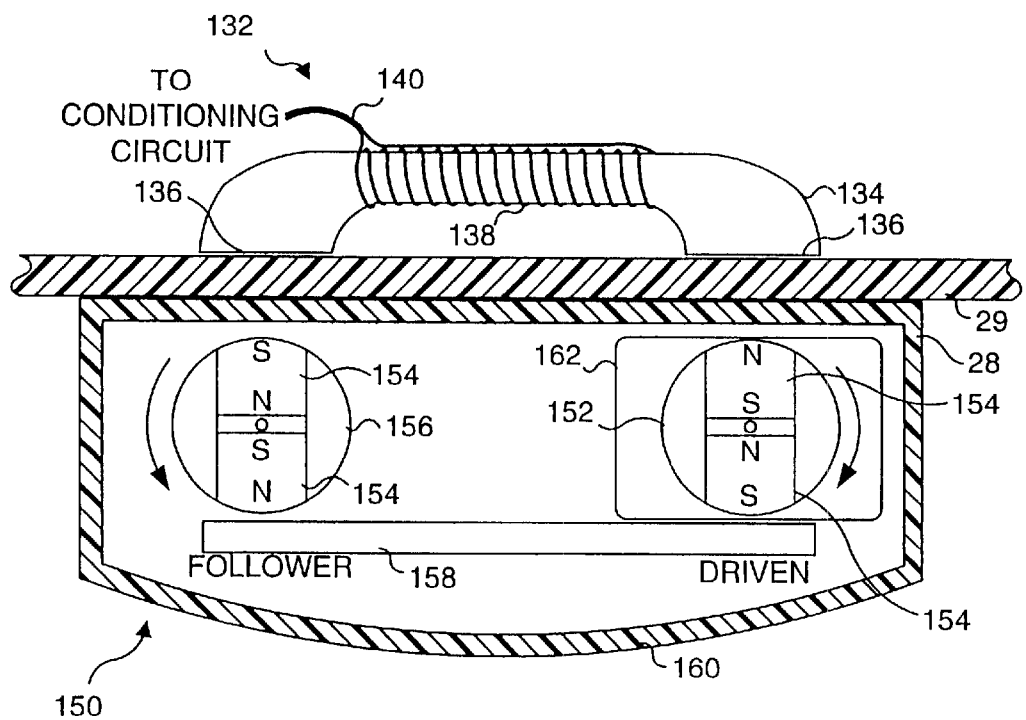
Figure 6B:
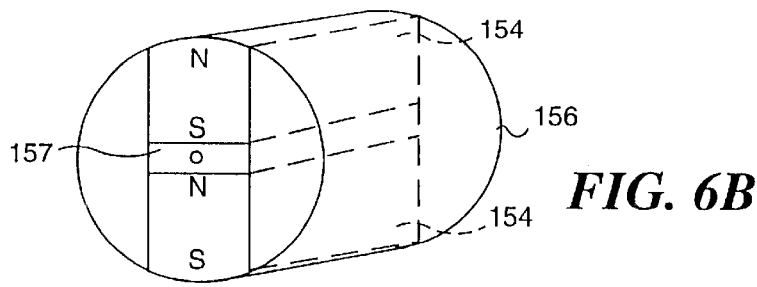
Figure 7:
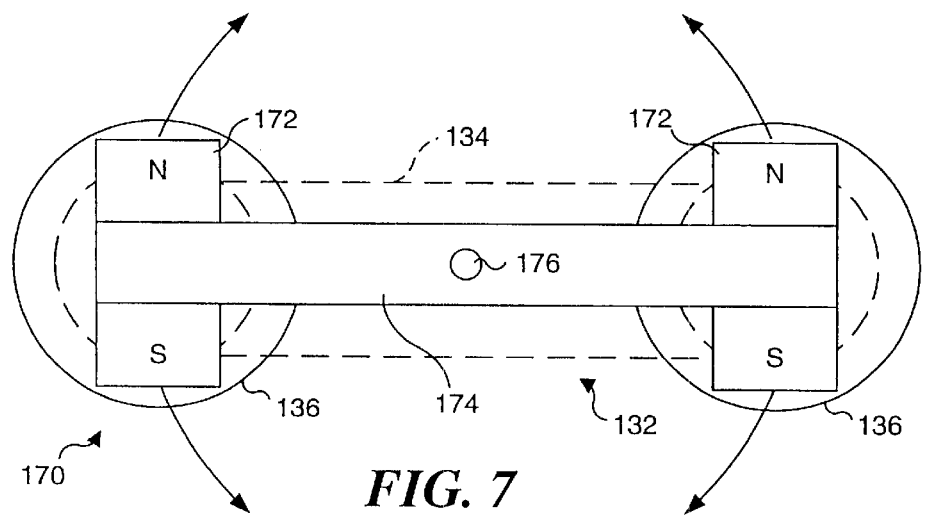
Figure 8:
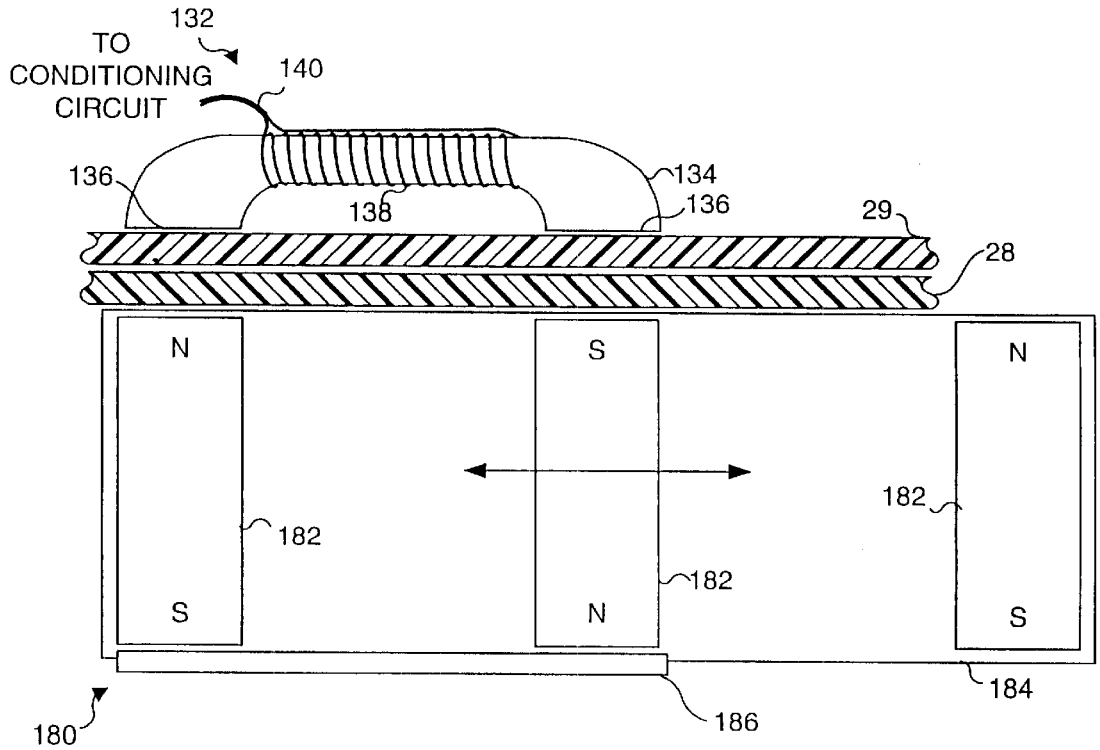
Figure 9:
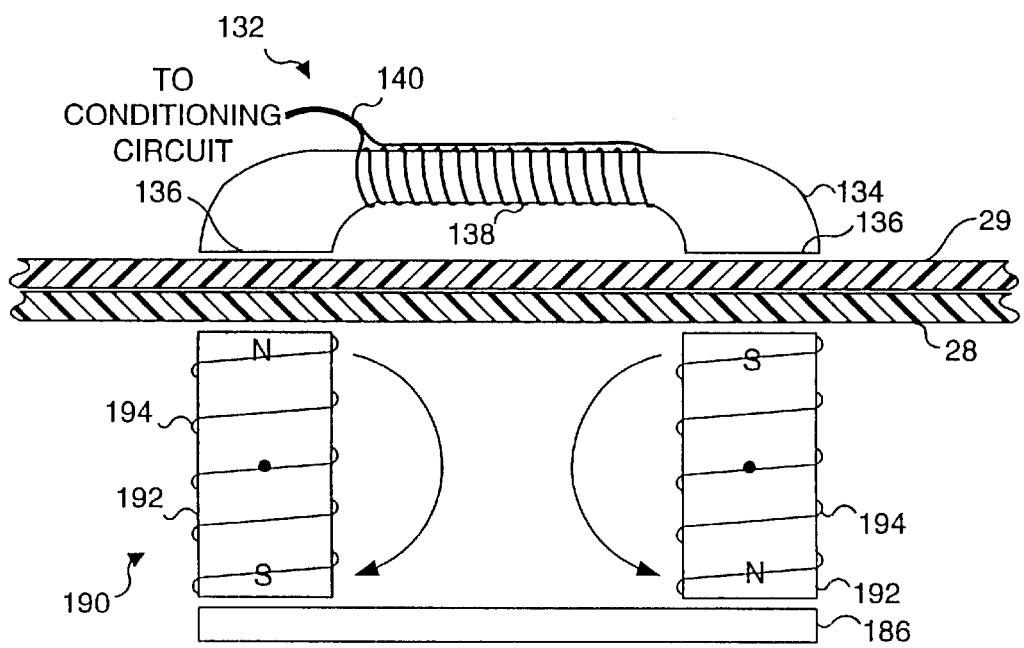
Figure 10:
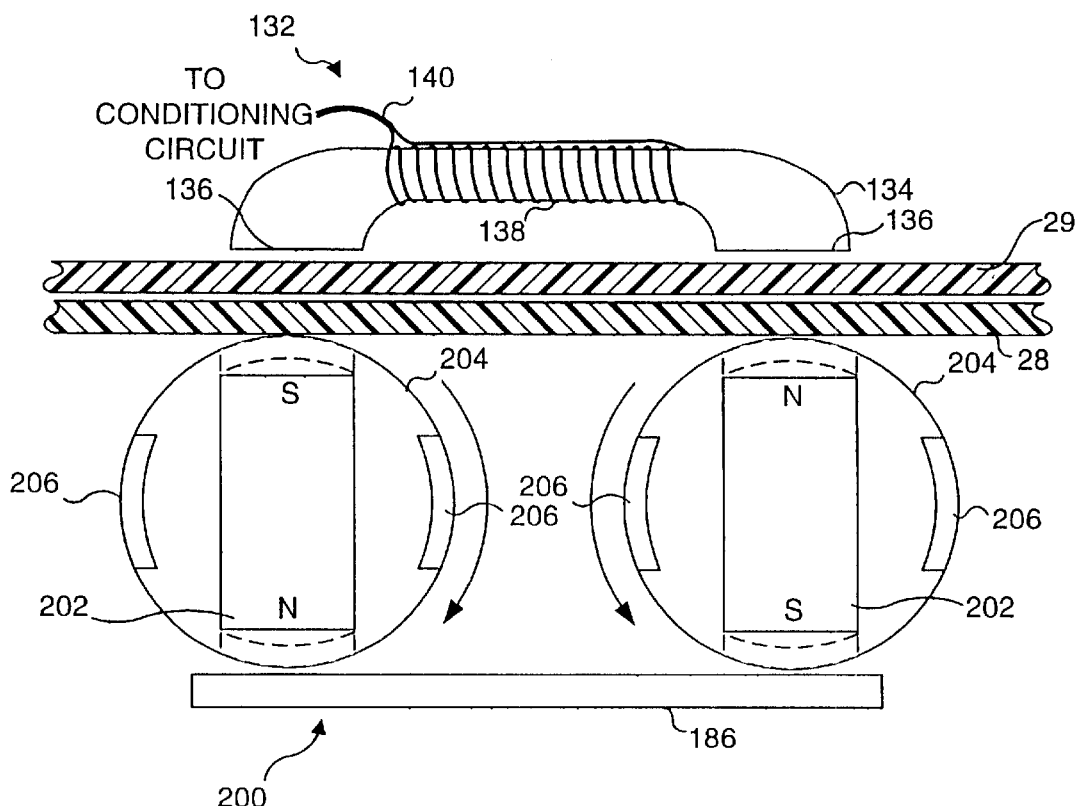
Figure 13A:
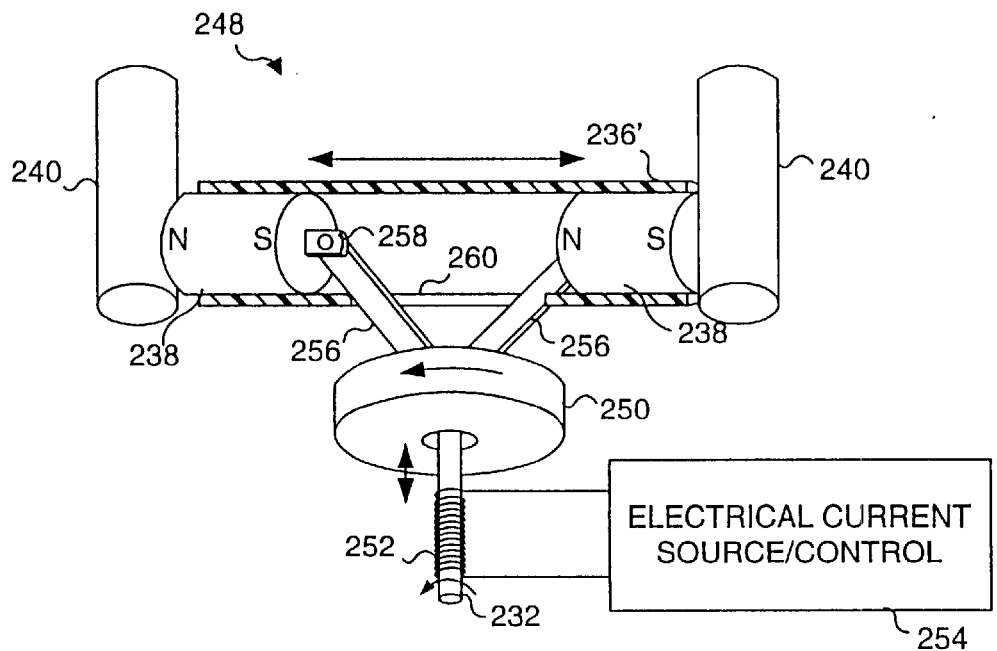
Figure 13B:
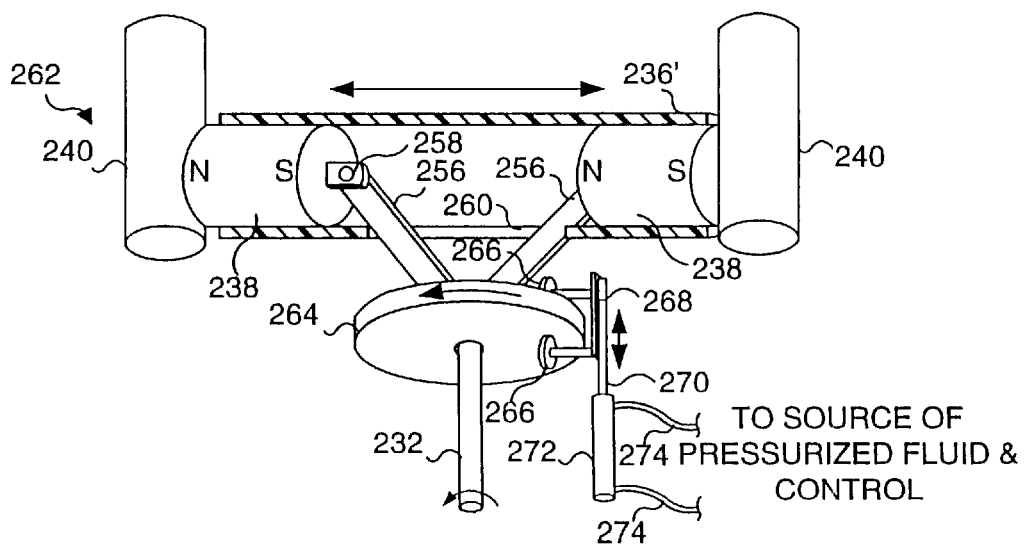
Figure 14:
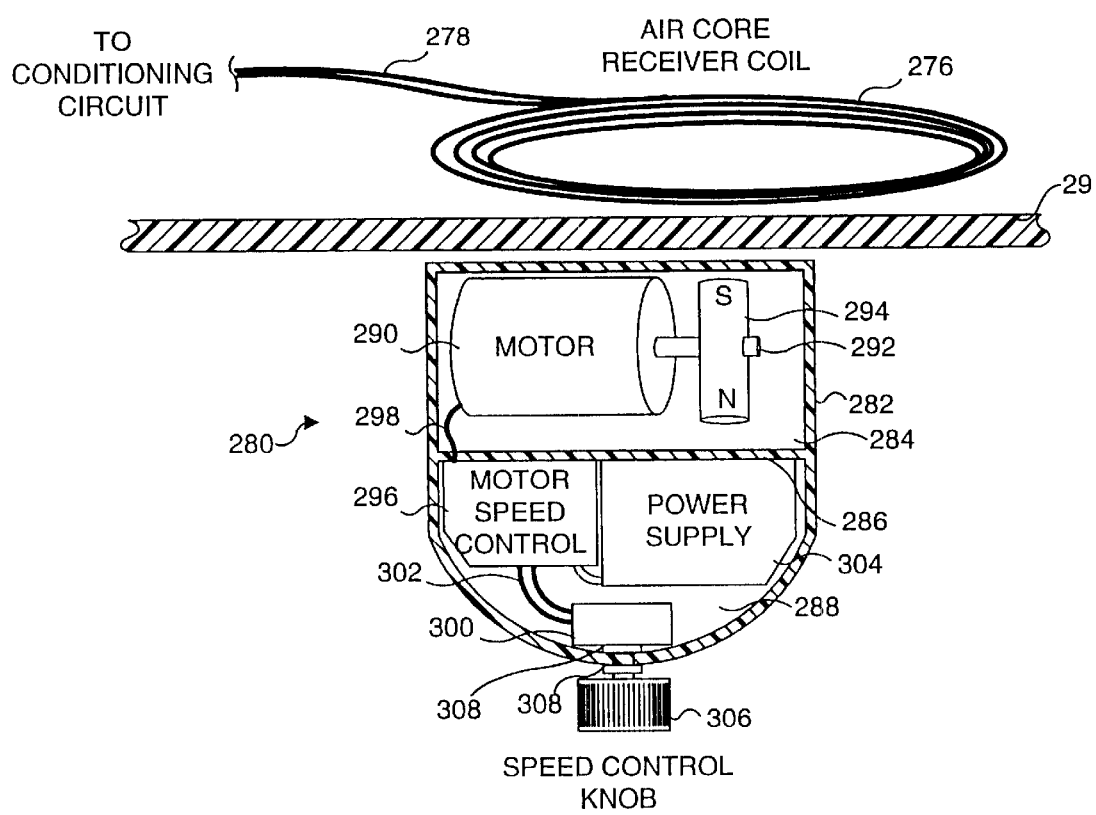
Figure 15A:
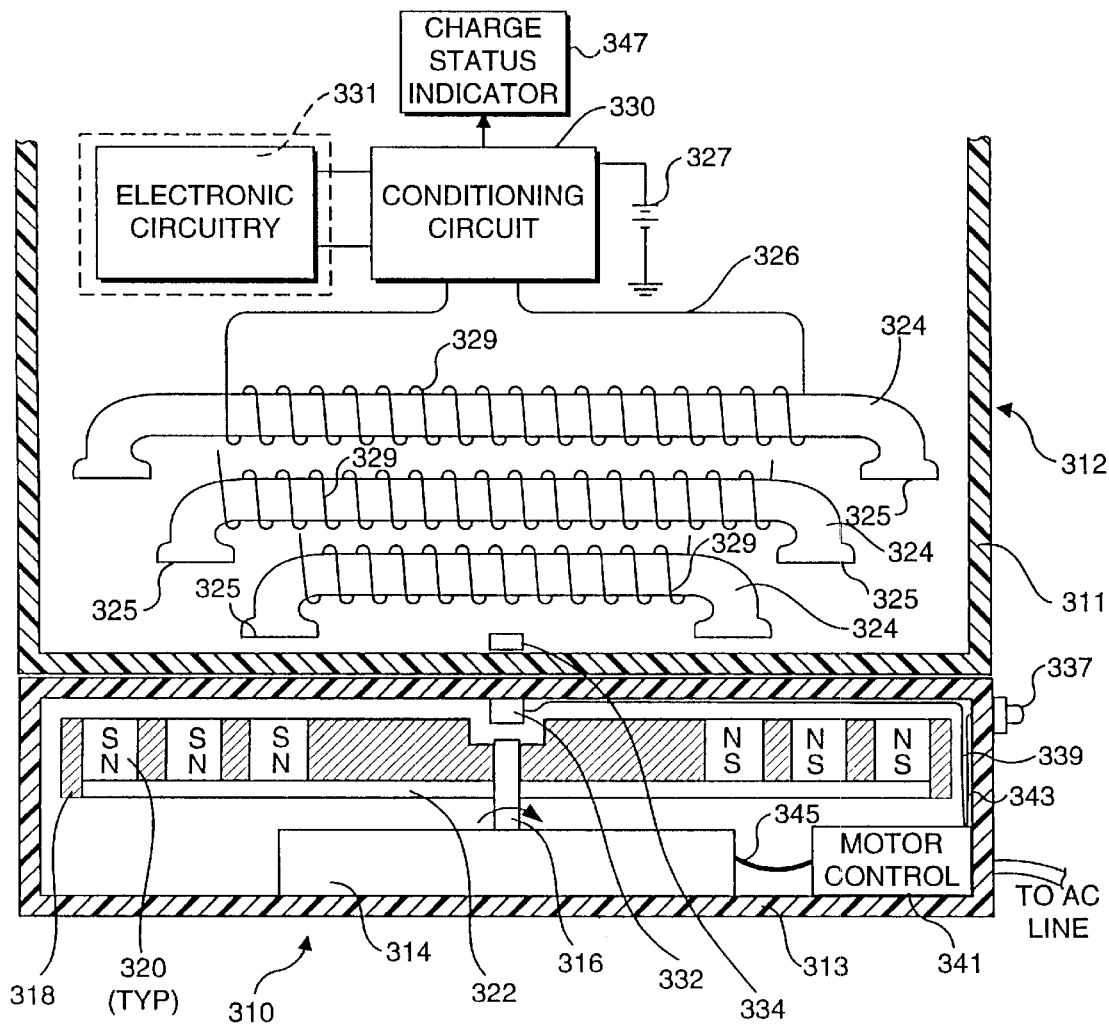
Figure 15B:
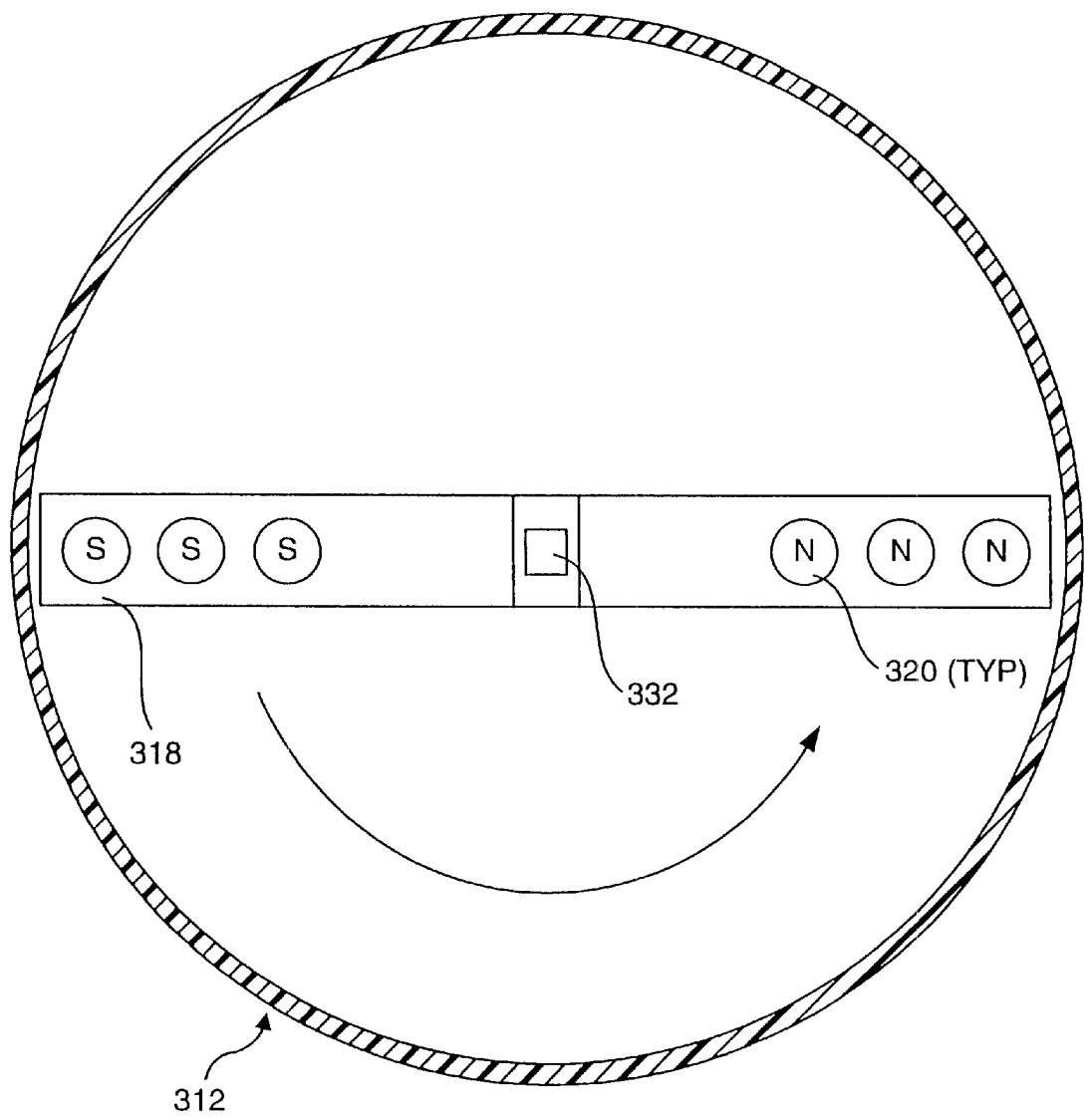
Figure 16:
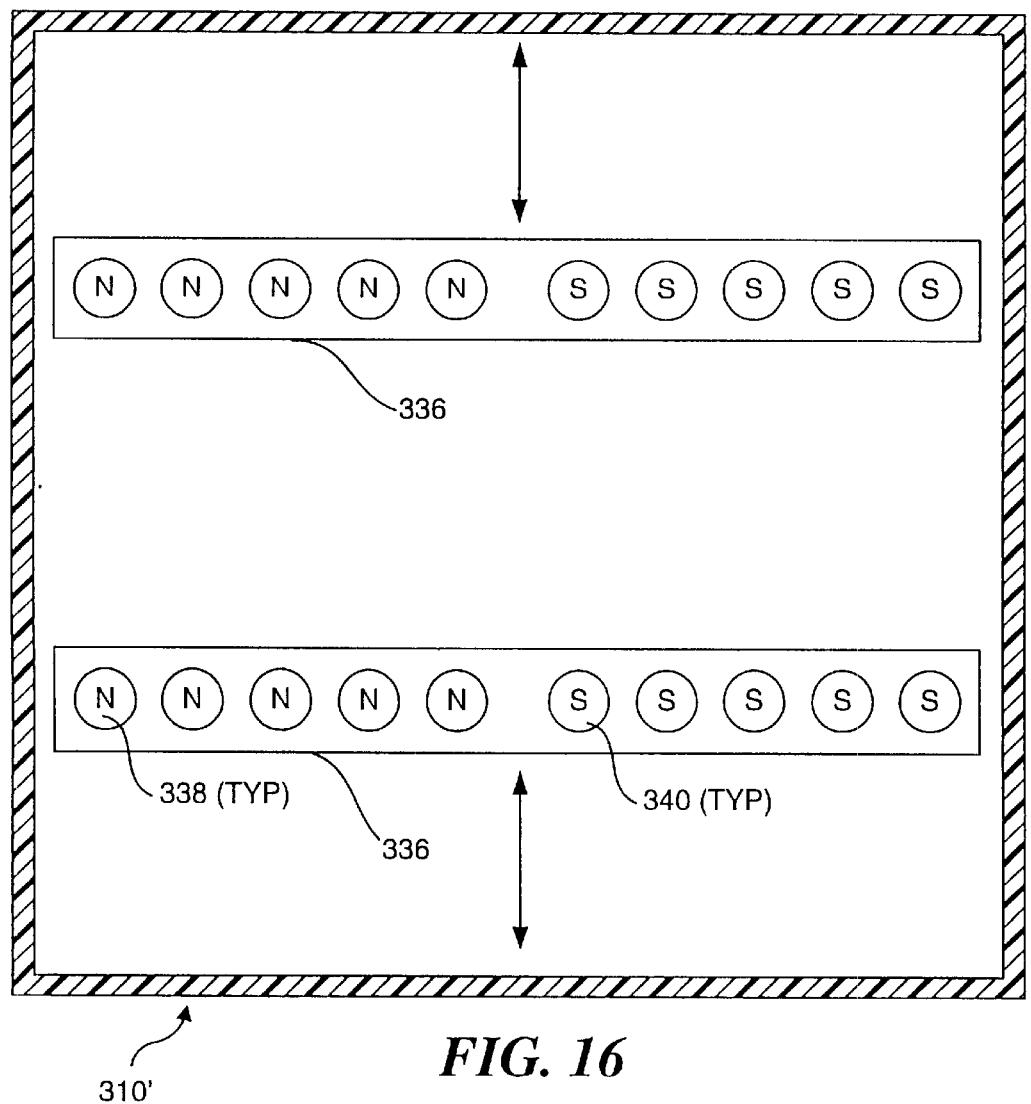
Figure 17:
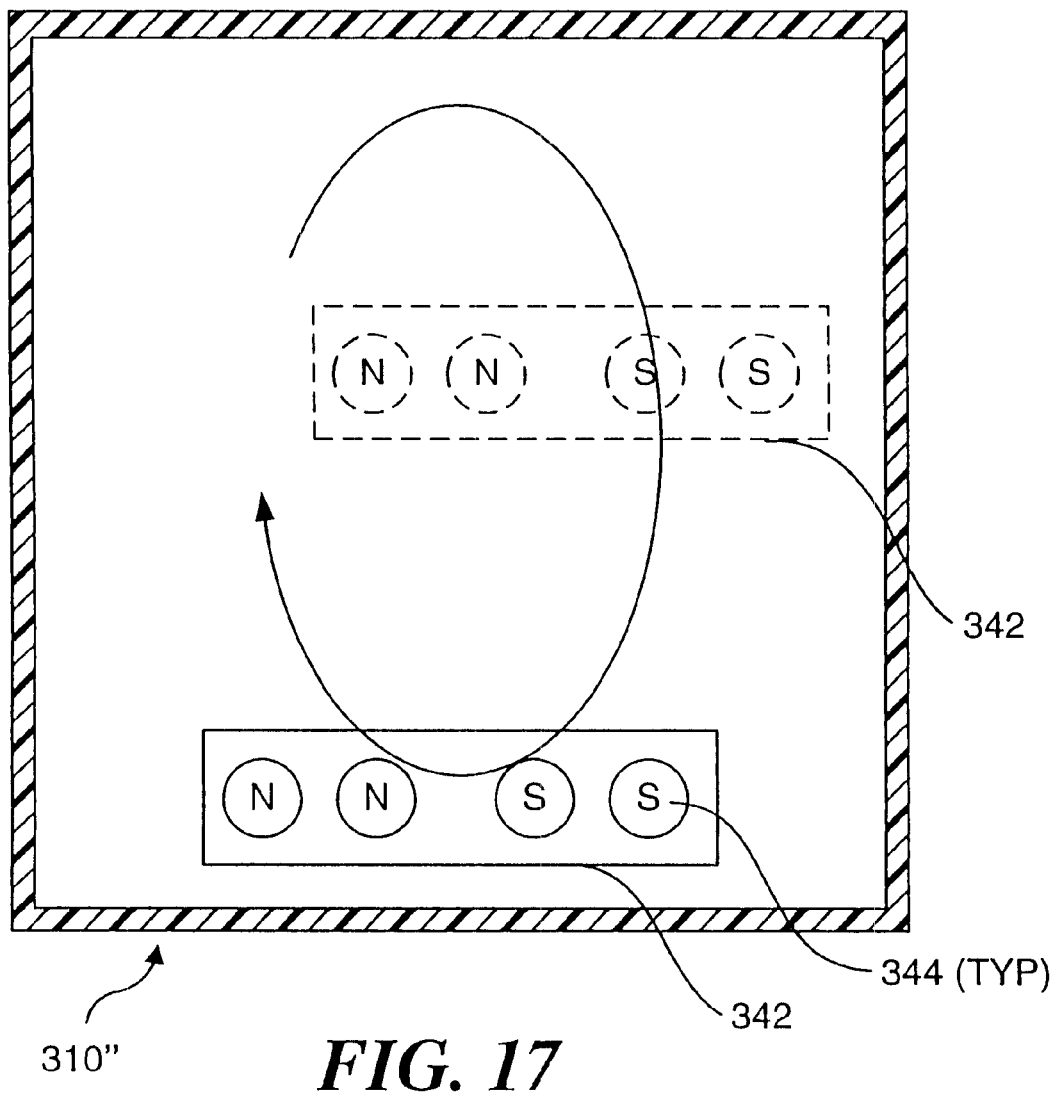
Figure 18A:
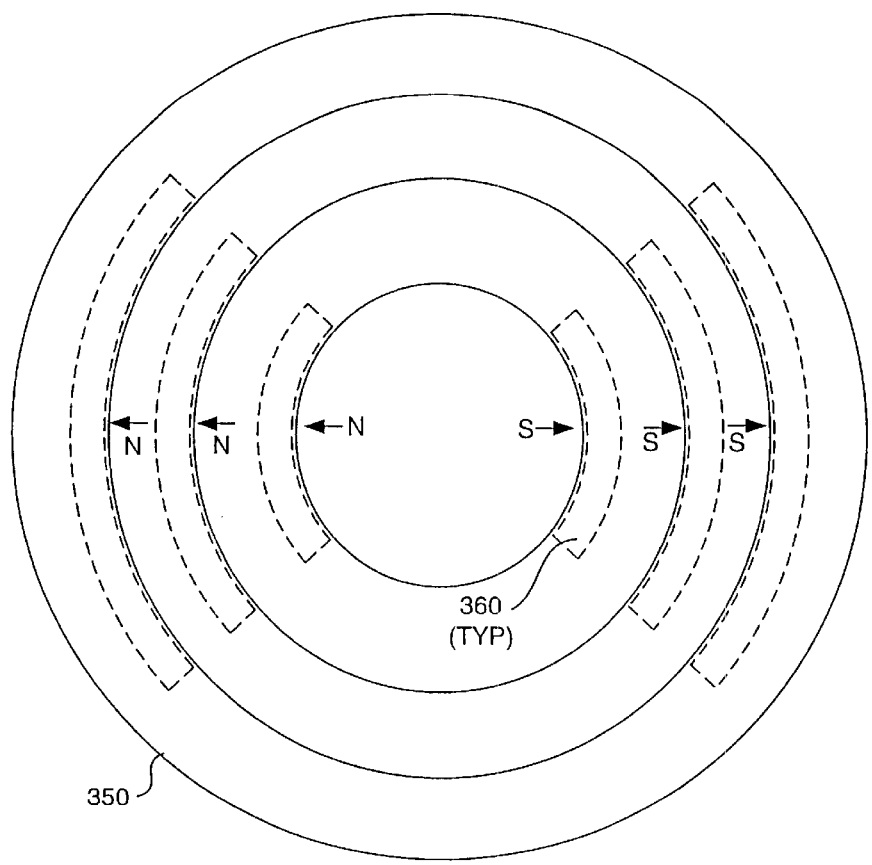
Figure 18B:
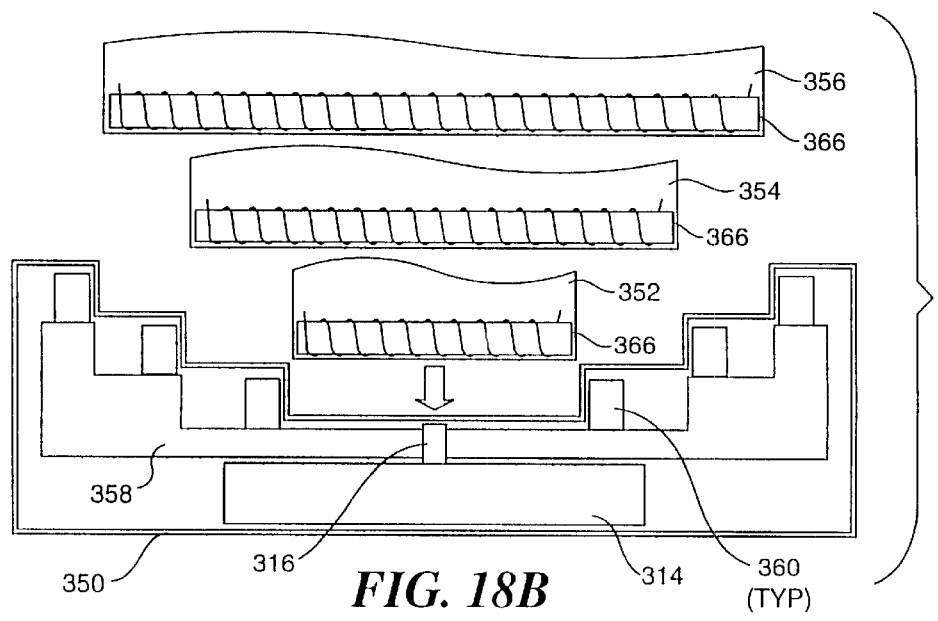
Figure 19A:
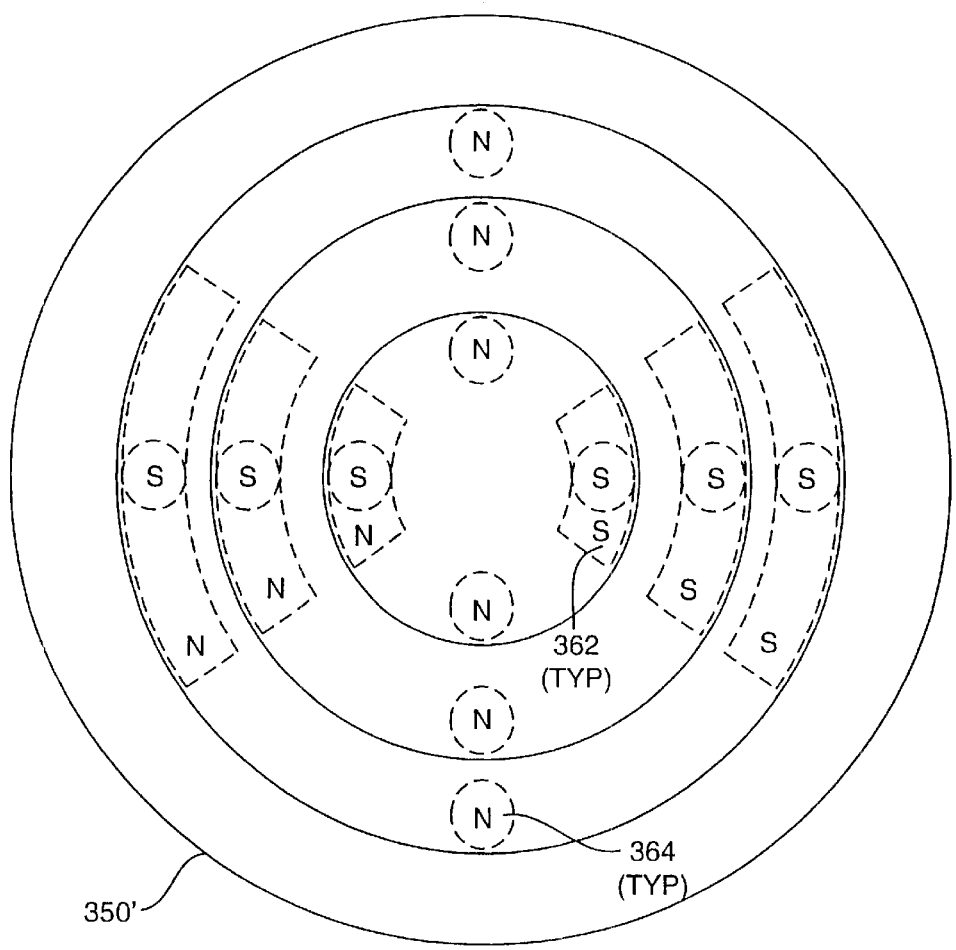
Figure 19B:
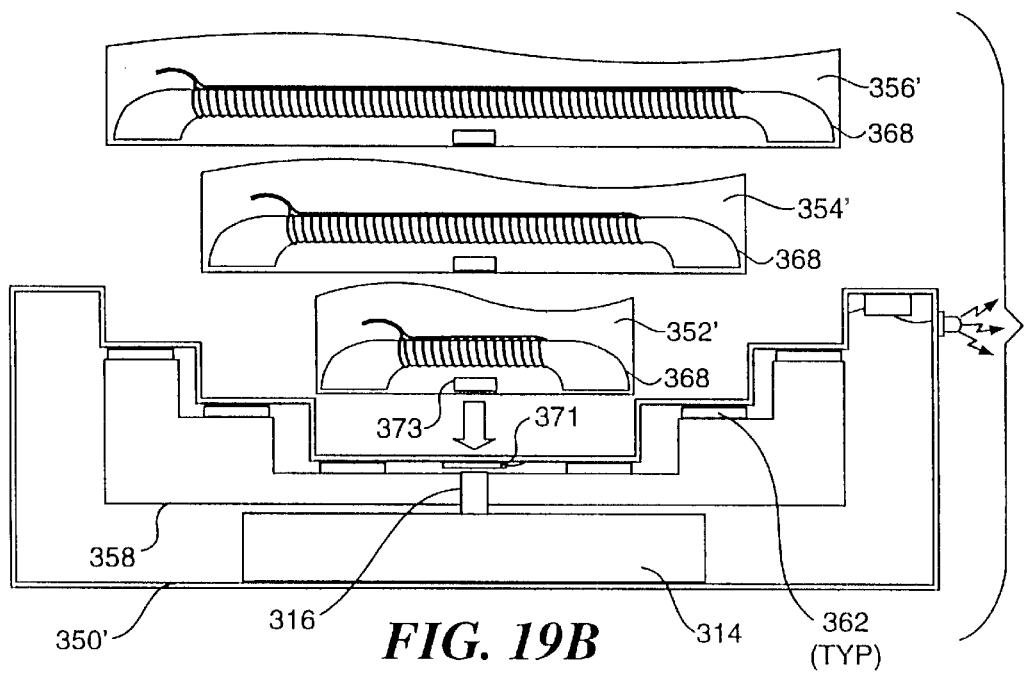

FIGS. 3A and 3B respectively illustrate a cross-sectional elevational view and a bottom view of a second embodiment of a flux generator base that includes two sets of permanent magnets;

FIG. 3C is an isometric bottom view of a driven disk for the flux generator, for use as a test prototype;

FIGS. 3D and 3D' are respectively a bottom view of the driven disk, with two permanent magnets, and a graph of related magnetic field intensity waveforms vs. time;

FIGS. 3E and 3E' are respectively a bottom view of the driven disk, with four permanent magnets, and a graph of related magnetic field intensity waveforms vs. time;

FIGS. 3F and 3F' are respectively a bottom view of the driven disk, with six alternating pole permanent magnets, and a graph of related magnetic field intensity waveforms vs. time;

FIGS. 3G and 3G' are respectively a bottom view of the driven disk, with six permanent magnets in an arrangement with three consecutive south pole faces and three consecutive north pole faces on the bottom of the drive disk, and a graph of related magnetic field intensity waveforms vs. time;

FIGS. 3H and 3H' are respectively a bottom view of a driven disk including a pair of arcuate-shaped permanent magnets, and a graph of related magnetic field intensity waveforms vs. time;

FIGS. 4A and 4B are respectively a side elevational cross-sectional view of another embodiment of a flux generator base coupled to a receiver coil in which a rotating permanent magnet produces a magnetic flux that is coupled to the receiver coil by two flux linkage bars, and a cross-sectional view of the flux generator base taken along section lines 4B-4B in FIG. 4A;

FIG. 5 is a cross-sectional side elevational view of another embodiment of the flux generator base and the receiver coil, in which a drive wheel rotates two permanent magnets;

FIGS. 6A and 6B are respectively a cross-sectional view of yet another embodiment of the flux generator base and the receiver coil in which one permanent magnet is directly driven to rotate and another permanent magnet magnetically follows the rotation of the driven permanent magnet, and an enlarged view of the following permanent magnet;

FIG. 7 is a plan view of a flux generator base (housing not shown) in which two permanent magnets are driven to reciprocate back and forth above the receiver coil;

FIG. 8 is a side elevational view of a flux generator base (only a portion of the housing shown) in which three permanent magnets are driven to linearly reciprocate below the receiver coil;

FIG. 9 is a side elevational view of a flux generator base (only a portion of the housing shown) in which conductors coiled around two permanent magnets selectively vary a magnetic field produced by the permanent magnets;

FIG. 10 is a side elevational view of a flux generator base (only a portion of the housing shown) in which two rotating flux linkage tabs vary the magnetic flux linked between two fixed permanent magnets to the receiver coil;

FIGS. 11 and 11' are respectively an isometric view of a flux generator base (housing not shown) in which fixed permanent magnets and a rotating flux shunt bar are provided, and a graph of the current pulses vs. time produced in the receiver coil;

FIG. 12 is a side elevational view of the receiver coil and a flux generator base (only a portion of the housing shown) in which two permanent magnets are slidably supported within a rotating tube so as to minimize starting torque, and so as to reduce an external magnetic field (outside the housing) when the permanent magnets are not rotating;

FIGS. 13A and 13B are external power heads in which a force is applied by a solenoid coil/ring magnet, and by a fluid cylinder, respectively, to two permanent magnets that are slidably mounted in a rotating tube so as to minimize starting torque, and so as to reduce an external magnetic field (outside the housing) when the permanent magnets are not rotating;

FIG. 14 is a cut-away side elevational view of yet another flux generator base including a speed control and a permanent magnet that is drivingly rotated within a plane, which is generally transverse to the plane of an internal air core receiver coil disposed within the portable apparatus to be charged;

FIGS. 15A and 15B are respectively an elevational view and plan view of a universal charger base implementation of the present invention;

FIG. 16 shows an optional embodiment of the universal charger base of FIGS. 15A and 15B wherein a pair of flux-generating bars are moved in a linear motion;

FIG. 17 shows an alternative embodiment of the universal charger base of FIGS. 15A and 15B wherein a pair of flux-generating bars are moved in an elliptical motion;

FIGS. 18A and 18B are respectively a plan view and a cut-away side elevational view of a universal charger base that provides a stepped mounting interface for use with various-sized receiver units; and FIGS. 19A and 19B are respectively a plan view and a cut-away side elevational view of yet another alternative embodiment of a universal charger base that provides a stepped mounting interface for use with various-sized receiver units.

DESCRIPTION OF THE PREFERRED EMBODIMENTS

Figure 1:
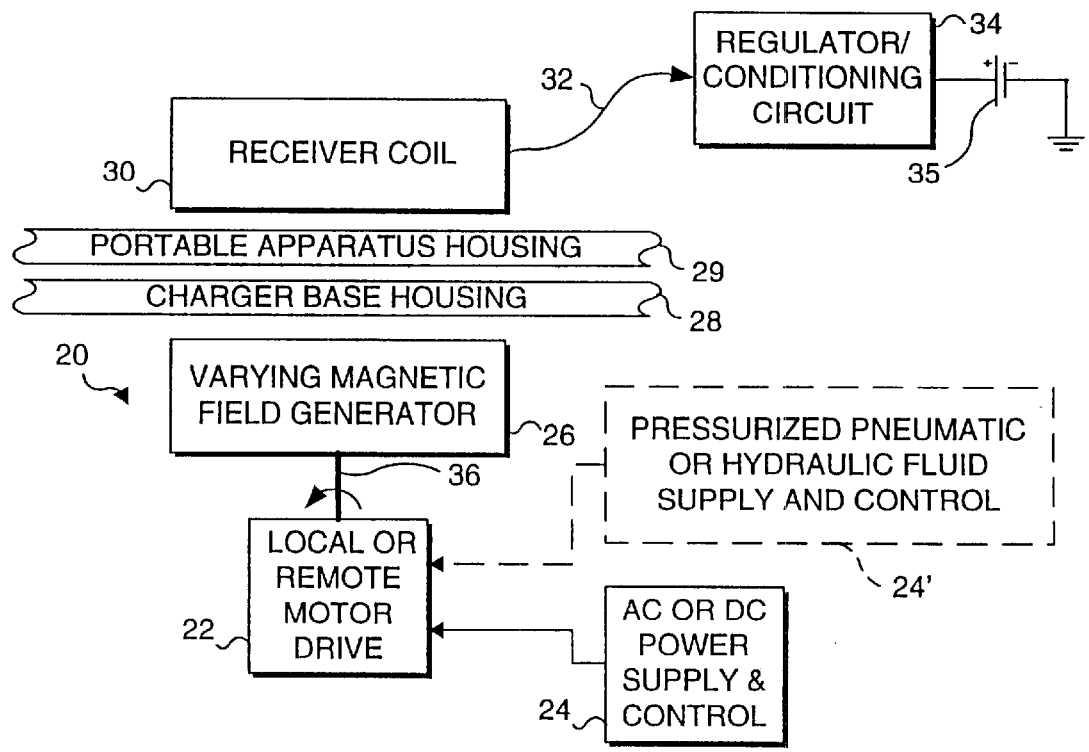
FIG. 1 is a block diagram illustrating the primary components of the present invention.

With reference to FIG. 1, a block diagram shown therein illustrates a typical application of the present invention. In this application, a flux generator base 20 includes a local (or remote) motor drive 22 that is energized from a power supply/control 24. Local (or remote) motor drive 22 comprises a prime mover that supplies a mechanical driving force to actuate a varying magnetic field generator 26. While the motor drive is preferably electrical, it is also contemplated that a pneumatic or hydraulic motor can alternatively be used as the prime mover. A pressurized pneumatic or hydraulic fluid supply and control 24' is shown for use in controlling such a motor. By using a fluid drive motor, electrical current to and in the device is eliminated, which may be desirable in certain applications. However, an electrically powered motor is typically lower in cost and generally preferable. To provide electrical current to operate an electrical motor, power supply/control 24 is preferably energized by connection to an AC line source (not separately shown). However, a DC battery supply might be used in certain applications, for example, when power is provided by connection to an automotive electrical system. It is also contemplated that a hand crank (not shown) can be employed for actuating varying magnetic field generator 26.

If the mechanical driving force for actuating varying magnetic field generator 26 is provided locally, the motor drive is coupled to the varying magnetic field generator through a drive shaft 36. Conversely, if the motor drive is disposed at a remote point, separate from the varying magnetic field generator, the mechanical driving force can be provided through a flexible cable (not separately shown) that extends between the remote motor drive and varying magnetic field generator 26. The movement produced by the motor drive causes a variation in the magnetic field produced by magnetic field generator that changes the magnetic flux through a path outside of flux generator base 20.

Flux generator base 20 is intended to produce a varying magnetic field that induces a corresponding electrical current to flow in a conductor. The conductor is disposed sufficiently close to the flux generator base to enable magnetic coupling between the conductor and the flux generator to occur. In one preferred application of the flux generator base, the varying magnetic field it produces passes through a housing 28 in which the varying magnetic field generator is disposed and a separate housing 29 in which the rechargeable battery is stored, and couples with a receiver coil 30 that is positioned inside housing 29, directly opposite varying magnetic field generator 26. Preferable, housings 28 and 29 comprise material through which magnetic flux readily passes, such as a plastic, fiberglass, or a composite. A typical separation between varying magnetic field generator 26 and receiver coil 30 is from about 0.5 cm to about 2.0 cm.

Receiver coil 30 is connected to a conditioning circuit 34 through a lead 32, which conveys the electrical current induced in the receiver coil by the varying magnetic field; this electrical current is then appropriately regulated by the conditioning circuit to achieve a voltage and current appropriate to recharge the battery (or batteries) connected thereto.

The conditioning circuit may be used to energize a storage battery or storage capacitor for storing energy coupled to receiver coil 30. Alternatively, a battery or capacitor for storing energy (neither shown) may be disposed at the receiver coil. It will also be apparent that the portable apparatus can be directly energized using the present invention, in which case, an energy storage device need not be provided.

Figure 2:
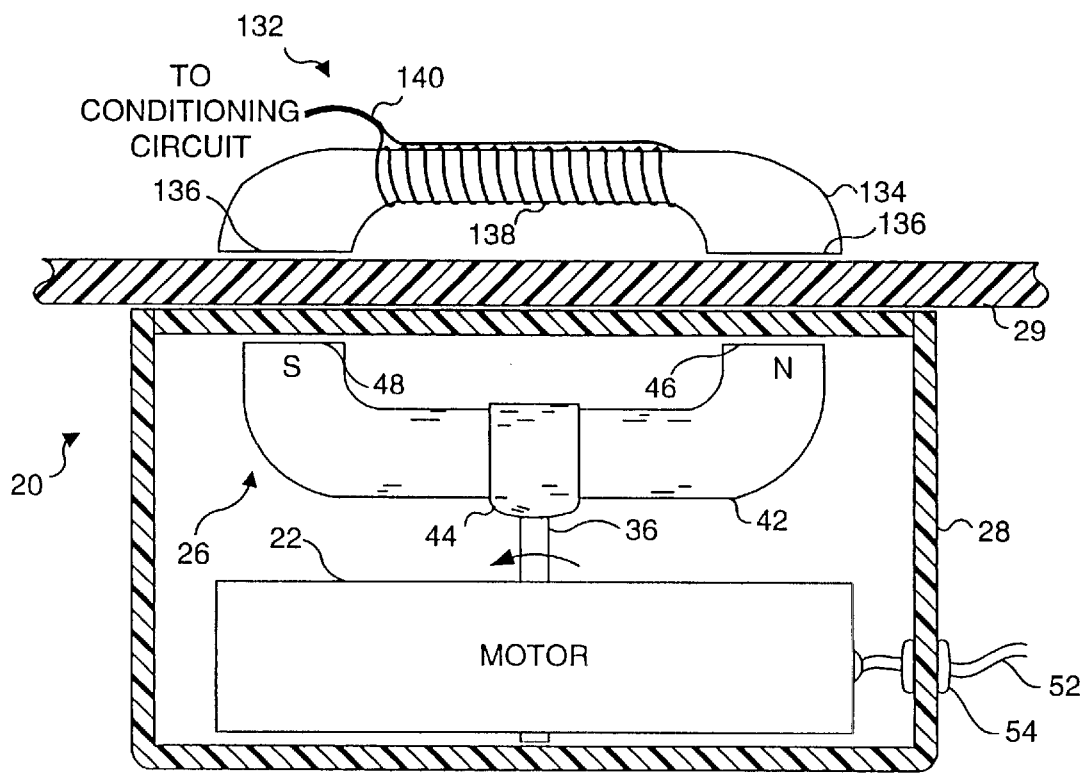
FIG. 2 is a cross-sectional view of a first embodiment of a flux generator base for coupling a varying electromagnetic flux into a receiver coil in a receiving unit, in accord with the present invention.

FIG. 2 illustrates a first embodiment of flux generator base 20 in which motor drive 22 is disposed within housing 28 of the flux generator base. Motor drive 22 is coupled to a generally elongated U-shaped permanent magnet 42 through rotating drive shaft 36. The rotating drive shaft connects to a collar 44 around the midsection of permanent magnet 42. Preferably in this and in each of the other embodiments of the present invention described below, the permanent magnet is formed of a neodymium-iron-boron alloy or other rare earth or metal alloy that produces a relatively high magnetic flux density. Other types of ferro-magnetic alloys are also acceptable for this purpose, although it is generally desirable to use a material for the permanent magnets that produces a relatively strong magnetic field in the present invention. Permanent magnet 42 includes a north pole face 46 and a south pole face 48 that face upwardly and are disposed immediately adjacent the interior side of the lower surface of housing 28 (as depicted in the Figure—it will be noted that only the relative orientation of the components is important, not their absolute orientation). To prevent undesired shunting of the magnetic flux between north pole face 46 and south pole face 48 and eddy current losses that would occur if a conductive material were used, housing 28 preferably comprises a plastic polymer material that is a good electrical insulator and does not block the magnetic flux produced by the permanent magnet. In instances where the motor drive comprises an electric motor, an electrical current appropriate to energize the motor drive is supplied by electrical leads 52, which run through a grommet 54 disposed in the side of housing 28.

FIGS. 3A and 3B show an alternative embodiment, illustrating a varying magnetic field generator 60. In these Figures, the housing and motor drive of the charger are not illustrated, but it will be apparent that a housing such as housing 28 can enclose varying magnetic field generator 60. A local or a remote motor drive is coupled to a drive shaft 64 to rotate a disk 62, which comprises the varying magnetic field generator, in either direction about a longitudinal axis of drive shaft 64. Embedded within disk 62 are two sets of permanent magnets 66 and 68; the north pole face of one of these permanent magnets and the south pole face of the other permanent magnets are generally flush with the lower surface of disk 62 (as shown in the Figure). A flux linkage bar 70 extends between the south and north pole faces of permanent magnets 66 (within disk 62), while a flux linkage bar 72 extends between the north and the south pole faces of permanent magnets 68 (within disk 62). The relationship of the permanent magnets and flux linkage bars are best illustrated in FIG. 3B.

Rotation of disk 62 about its central axis in either direction varies the magnetic field experienced at receiver coil 30 (shown in FIG. 1) and alternately changes the polarity of the field as the different permanent magnets rotate to positions adjacent to the pole faces of the receiver coil. The varying magnetic field that is thus produced by rotation of disk 62 induces a generally corresponding varying electrical current in the receiver coil that is usable to energize a device such as a portable hand tool. Preferably, the electrical current supplied to the device is first conditioned by conditioning circuit 34 (also shown in FIG. 1), for example, to rectify, filter, regulate the current. The speed at which disk 62 rotates changes the frequency of the induced electrical current and also varies the average magnitude of the electrical current induced in the receiver coil. It is contemplated that disk 62 can be rotated at a rate such that the frequency of the current induced in the receiver coil is within the range from less than 10 Hz to more than 10 kHz.

It should be noted that the power transferred to the receiver coil increases as the rotational speed of the varying magnetic field generator increases. Also, as the relative spacing between varying magnetic field generator 60 and the receiver coil changes, the amplitude of the induced electrical current also changes, i.e., the magnitude of the induced electrical current increases as the separation decreases. While not shown in any of the Figures, it will be apparent that the elevation of rotating disk 62 above the receiver coil can be readily changed to modify the respective separation between the two devices and thereby selectively determine the maximum current induced in the receiver coil— all other parameters such as rotational speed remaining constant.

FIGS. 3D-3G show further embodiments of the varying magnetic field generator of the type illustrated in FIGS. 3A and 3B. The disk configuration for the varying magnetic field generator illustrated in these Figures was first used to confirm the effectiveness of the present invention. In FIG. 3C, a disk 62' is shown without any permanent magnets. In an embodiment 60' shown in FIG. 3D, only two permanent magnets 75 and 76 are inserted within disk 62', and other cavities 74 in disk 62' do not contain permanent magnets. As shown in the Figure, permanent magnet 75 is positioned within disk 62' with its north pole face facing downwardly, flush with the lower surface of the disk, while permanent magnet 76 is positioned with its south face facing downwardly, flush with the lower surface of the disk. The opposite pole faces of each of permanent magnets 75 and 76 are directed upwardly, and the longitudinal axes of the permanent magnets are generally aligned parallel with the axis of drive shaft 64.

To test the efficacy of the embodiments shown in FIGS. 3D-3G, drive shaft 64 was simply chucked in a drill press (not shown) and rotated so that the lower surface of the disk in which the permanent magnets are embedded passed immediately above a receiver coil (generally like receiver coil 132—shown in FIG. 2). Using only one permanent magnet 75 and one permanent magnet 76 as shown in FIG. 3D, the magnetic field intensity waveforms illustrated in the graph of FIG. 3D' were produced, which include positive pulses 78 and negative pulses 80.

When two permanent magnets 75 and two permanent magnets 76 were disposed opposite each other as shown in FIG. 3E, rotation of a disk 62' induced magnetic field intensity waveforms comprising two positive pulses 82 followed by two negative pulses 84 in repetitive sequence, as shown in FIG. 3E'. Alternating permanent magnets 75 and 76 in each of the cavities formed in a disk 62''' to produce a varying magnetic flux generator 60''' as shown in FIG. 3F, produced higher frequency magnetic field intensity waveforms, including positive pulses 86 and negative pulses 85, which are more sinusoidal, as indicated in FIG. 3F''''. In the embodiment of varying magnetic field generator 60'', shown in FIG. 3G, three permanent magnets 75 are disposed adjacent each other with their north pole faces flush with the lower surface of a disk 62'''', while three permanent magnets 76 have the south pole face flush with the lower surface of the disk. Rotation of disk 62'''' produced the magnetic field intensity waveforms shown in FIG. 3G', which include three positive pulses 88 followed by three negative pulses 90, in repetitive fashion.

In FIG. 3H, a disk 87 includes two generally arcuate-shaped permanent magnets 89 and 91 disposed adjacent radially opposite sides of the disk, with the north pole of permanent magnet 89 and the south pole of permanent magnet 91 flush with the lower surface of the disk (as shown in the Figure). A flux linkage bar 93 extends across the disk, over the opposite poles of the two permanent magnets. Due to the arcuate shape of the permanent magnets, they extend over a larger portion of the rotational arc of disk 87, causing generally sinusoidal magnetic field intensity waveforms 95 and 99 to be magnetically induced in the receiver coil, as shown in FIG. 3H'.

At relatively slow rotational speeds, the rotation of one or more very strong permanent magnets directly below a receiver coil may apply sufficient torque to the receiver coil to cause the receiver coil to move back and forth slightly. However, any movement or vibration of the receiver coil due to such torque will be substantially eliminated when the receiver coil is attached to the device that is to be energized or which includes a battery to be charged by the present invention. Furthermore, if the rotational speed of the varying magnetic field generator is sufficiently high, the effects of any torque applied to the receiver coil will be almost imperceptible.

In FIGS. 4A and 4B, a flux generator base 92 is illustrated that eliminates virtually all torque on the receiver coil. In this embodiment, a permanent magnet 94 is coupled through a connection 102 to a flexible cable 100, which turns within a flexible drive shaft 97. Flexible cable 100 is connected to a remote electrical drive motor (not shown in this Figure) that applies a rotational driving force to the flexible drive shaft. The flexible drive shaft rotates within a bearing 96 that is supported in a cylindrical-shaped housing 104 of flux generator base 92. Cylindrical-shaped housing 104 preferably is fabricated of a plastic polymer that does not block or shunt magnetic flux and which does not conduct eddy currents. Inside cylindrical-shaped housing 104, at diametrically opposite sides of the housing, are disposed two vertically aligned flux linkage blocks 98. As permanent magnet 94 rotates, its north and south poles pass adjacent to the top inwardly facing surfaces of flux linkage blocks 98, as shown clearly in FIG. 4B. The magnetic flux produced by permanent magnet 94 is conveyed through the flux linkage blocks and coupled into an overlying receiver coil 132. Flux generator base 92 is disposed relative to receiver coil 132 such that the upper ends of the flux linkage blocks are disposed opposite core faces 136 of the receiver coil. Since permanent magnet 94 rotates in a plane that is substantially spaced apart from the top of cylindrical-shaped housing 104 (as illustrated in the Figure), the permanent magnet applies substantially less attraction to the overlying receiver coil than would be the case if the permanent magnet were rotating in a plane closer to the receiver, e.g., immediately adjacent to the top of the cylindrical-shaped housing. Furthermore, flux linkage blocks 98 tend to concentrate the magnetic flux produced by the rotating permanent magnet in a vertical direction, minimizing any horizontal component of the magnetic flux, so that little rotational force is experienced by adjacent core faces 136 of receiver coil 132.

Referring now to FIG. 5, another embodiment comprising a flux generator base 110 is disclosed. In flux generator base 110, two cylindrical permanent magnets 124 are provided, each of which rotate around shafts 130 that extend through their respective centers. Alternatively, more conventional bar-shaped permanent magnets mounted in a plastic polymer cylinder can be used. Mechanical link bars 118 are attached to each of the permanent magnets at pivot points 122 and extend to a common pivot point 120 on a rotating driven wheel 114 that is disposed midway between the two permanent magnets. Driven wheel 114 is rotated by a drive shaft 116 that is connected to an electrical drive motor (not shown) disposed either within flux generator base 110, or alternatively, at a more remote location, as discussed above. Since pivot point 120 is offset from drive shaft 116, i.e., offset from the center of the driven wheel 114, movement of pivot point 120 due to rotation of the driven wheel is translated by mechanical link bars 118 into a corresponding rotational force applied to pivot points 122 that causes permanent magnets 124 to rotate about their shafts 130. As corresponding north and south poles on permanent magnets 124 move to positions immediately adjacent a curved flux linkage bar 126, the opposite poles of the permanent magnets are disposed adjacent vertically aligned flux linkage bars 128. In this Figure, the lower ends of the flux linkage bars are disposed adjacent the top of flux generator base 110, spaced apart and directly opposite core faces 136 of a core 134 comprising receiver coil 132. This core is fabricated of a metal or alloy having a relatively high magnetic permeability. Coiled about core 134 are a plurality of turns 138 of an electrical conductor, the ends of which comprise a lead 140, which extends to the conditioning circuit (not shown in this Figure) that rectifies, filters, and regulates the current from receiver coil 132, as required by the device in which the receiver coil is installed. The varying magnetic flux applied to receiver coil 132 induces a corresponding varying electrical current to flow through turns 138 and through lead 140.

Another embodiment of a flux generator base 150 is illustrated in FIG. 6A. In this embodiment, a driven wheel 152, fabricated of a plastic polymer or other suitable non-magnetic material bonded to a pair of permanent magnets 154, is rotated by a motor drive 162. Magnetic flux from permanent magnets 154 is coupled through a horizontally extending flux linkage bar 158 disposed below the driven wheel (as shown in the Figure) to a follower wheel 156, which also includes a pair of permanent magnets 154 bonded together with their respective north and south pole faces facing each other, separated by a flux linking section 157, best seen in FIG. 6B. (The structure of driven wheel 152 is substantially identical to that of follower wheel 156.) Rotation of driven wheel 152 causes a varying magnetic field polarity to be experienced by permanent magnets 154 on follower wheel 156 and the interaction with this magnetic field rotates the follower wheel generally in lock step with the rotation of driven wheel 152. As a consequence, magnetic flux from the pairs of permanent magnets 154 on the driven wheel and follower wheel couple into receiver coil 132, inducing an electrical current to flow in turns 138 for use in energizing a portable device or charging its batteries.

The embodiments of flux generator bases discussed thus far have all included permanent magnets that rotate. In FIG. 7, a flux generator base 170 is illustrated that includes a flux linkage bar 174 mounted to a shaft 176. Shaft 176 reciprocatively rotates back and forth, causing permanent magnets 172 to pass back and forth above core faces 136 of receiver coil 132. As the magnetic flux produced by the permanent magnets and experienced by receiver coil 132 periodically changes due to the reciprocating movement of the permanent magnets back and forth below the pole faces of the receiver coil, an electrical current is induced to flow within the turns of the conductor (not shown in FIG. 7) wrapped around core 134. This electrical current is typically rectified, filtered, and regulated to meet the requirements of the device coupled to the receiver coil.

Instead of being rotatably reciprocated back and forth, the permanent magnets can be driven to move back and forth in a linear fashion, as in the embodiment of a flux generator base 180 illustrated in FIG. 8. In this embodiment, a flux shunt bar 186 is disposed below three vertically-aligned and spaced-apart permanent magnets 182 and extends over the respective north and south poles of two of the permanent magnets. The downwardly facing poles of permanent magnets 182 are respectively south, north, and south (or each can be of opposite polarity), in the order in which they are attached to a moving plate 184 that is reciprocatively driven back and forth. The spacing between permanent magnets 182 is such that at the two extreme linear positions of reciprocating plate 184, the poles of two of the permanent magnets are disposed immediately below core faces 136 on receiver coil 132; these poles are opposite in polarity. Linear reciprocating movement of reciprocating plate 184 is provided by an appropriate drive mechanism (not shown), receiving its motive power from an electrical motor drive (also not shown), which is disposed either locally with the flux generator base, or remotely and coupled to the flux generator base by a drive shaft.

In FIG. 9, an embodiment of a flux generator base 190 is illustrated that includes provision for selectively electrically controlling the strength of the magnetic field coupled to receiver coil 132. In this embodiment, instead of varying the separation between rotating permanent magnets 192 and receiver coil 132, an electrical conductor 194 is coiled around each of permanent magnets 192 and is coupled to a variable current power supply (not shown) that provides a direct current (DC) flowing through conductor 194. Note that permanent magnets 192 can be rotated about a common axis that is orthogonal to the axes of the rotation shown in the Figure. Since permanent magnets 192 are rotating, being driven by an electrical motor drive (also not shown in FIG. 9), conductor 194 must be coupled to the variable power supply using slip rings, brushes, a rotary transformer, or other suitable mechanism, as is commonly used for coupling power to a conductor on a rotating armature of an electric motor. The DC current passing through conductor 194 can either assist or oppose the magnetic field produced by permanent magnets 192, thereby selectively varying the strength of the magnetic field experienced by receiver coil 132 to control the magnitude of the electrical current that the receiver coil supplies to the conditioning circuit.

Another way to periodically vary the magnetic field experienced by receiver coil 132 is to periodically change the efficiency with which the magnetic flux produced by permanent magnets couples to the receiver coil. FIG. 10 illustrates one technique for varying the magnetic flux linkage between two permanent magnets 202 in a flux generator base 200 and the receiver coil. Permanent magnets 202 are stationary. A motor drive (not shown in this Figure) drivingly rotates two disks 204 that are disposed behind each of the fixed permanent magnets. Tabs 206 extend outwardly from the facing surfaces of disks 204 a distance equal to a little more than the thickness of permanent magnets 202 (measured in a direction normal to the plane of the paper in the Figure). Tabs 206 and disks 204 are fabricated of a metal or an alloy having a high magnetic permeability that provides enhanced flux linkage when disposed adjacent the poles of permanent magnets 202. A flux shunt bar 186 that is also fabricated of a material having a high magnetic permeability extends below permanent magnets 202 (as shown in this Figure), but is spaced sufficiently apart from the downwardly facing poles of the permanent magnets to provide clearance for tabs 206 to pass between the flux shunt bar and the poles of permanent magnets 202. As tabs 206 rotate between the lower poles of permanent magnets 202 and the upper surface of flux shunt bar 186, and between the upper poles of the permanent magnets and core faces 136 of receiver coil 132 (as shown by the dash lines that illustrate the tabs at those positions in phantom view), the flux linkage between permanent magnets 202 and core 134 greatly decreases so that substantially less magnetic field strength is experienced by the receiver coil. The magnetic flux produced by the permanent magnets is shunted through disks 204, with little of the magnetic flux flowing between the poles of the permanent magnets passing through the receiver coil. However, as disks 204 continue to rotate so that tabs 206 move to the positions shown by the solid lines in FIG. 10, the flux linkage between permanent magnets 202 and receiver coil 132 approaches a maximum. Thus, rotation of disks 204 causes core 134 to experience a varying magnetic field that induces an electrical current to flow within the conductor comprising turns 138.

As shown in FIG. 11, a further embodiment of the varying magnetic field generator includes a fixed flux linkage bar 225 and a rotating flux linkage shunt 214 connected to a drive shaft 212 that rotates the flux linkage shunt in a plane above the pole faces of permanent magnets 202 (as shown in the Figure), so that it passes between the pole faces of the permanent magnets and the pole faces of the receiver coil (not shown here). Fixed flux linkage bar 225 and rotating flux linkage shunt 214 are both fabricated of a metal or alloy with high magnetic permeability and thus characterized by its ability to substantially shunt magnetic flux. When rotating flux linkage shunt 214 is in the position represented by the phantom view (dash lines), i.e., in a position so that its longitudinal axis is oriented about 90° to the longitudinal axis of fixed flux linkage bar 225, the flux linkage between the permanent magnets and the receiver coil is at a maximum, and when the rotating flux linkage shunt is in the position shown (by the solid lines) in FIG. 11, the magnetic flux produced by the permanent magnets is substantially shunted between them through the rotating flux linkage shunt. Due to the resulting periodically varying magnetic flux coupled into the receiver coil core, an electrical current is induced in the receiver coil. FIG. 11' illustrates electrical current pulses 218 that are produced in the receiver coil as the flux linkage shunt rotates.

A desirable feature of the embodiments shown in both FIGS. 10 and 11 is that when the devices are de-energized, leaving the magnet flux shunted between the poles of the permanent magnets, very little magnetic field produced by the permanent magnets escapes outside the housing (not shown) around the flux generator base. The rotating flux linkage shunts thus serve to "turn off" much of the external magnetic field by shunting it between the poles of the permanent magnets.

When the electric motor used as the prime mover for any of the flux generator bases described above is initially energized to provide the rotational, pivotal, or linear reciprocating motion, the motor experiences a starting torque (that resists its rotation) because of the magnetic attraction between the permanent magnets and any flux linkage bar included in the flux generator base, and the receiver coil. FIG. 12 illustrates an embodiment for a flux generator base 230 that minimizes the starting torque experienced by the electrical motor. In this embodiment, a drive shaft 232 is coupled to a local or remotely disposed electrical motor drive 233. The lower end of drive shaft 232 is connected to a horizontally extending cylindrical tube 236. Permanent magnets 238 are supported within cylindrical tube 236 and are able to move radially inward or outward relative to the longitudinal axis of drive shaft 232. The permanent magnets are coupled to a helically-coiled spring 234 that extends between the permanent magnets, within the center of cylindrical tube 236, and applies a force that tends to draw the permanent magnets radially inward, away from the lower ends of flux linkage rods 240 (as shown in the Figure). When the motor drive that is coupled to drive shaft 232 is de-energized, permanent magnets 238 are thus drawn toward each other, minimizing the torque required to begin rotating cylindrical tube 236. However, after motor drive 233 is rotating drive shaft 232, the centrifugal force created by the rotation of the cylindrical tube overcomes the force of helical spring 234, causing permanent magnets 238 to slide radially outward, away from the central axis of drive shaft 232, until the permanent magnets reach stops (not shown) that limit their radial travel, so that their poles are closely spaced apart from flux linkage rods 240. A varying magnetic flux linkage with receiver coil 132 is then achieved.

In FIGS. 13A and 13B, two alternative techniques are shown for minimizing startup torque. However, a further advantage is provided by these alternatives, since they enable the magnitude of the current produced by the receiver coil to be controlled by varying the spacing between permanent magnets 238 and flux linkage rods 240 when the permanent magnets are rotating past the flux linkage rods. Specifically, as the spacing between the permanent magnets and flux linkage rods is increased, both the coupling of magnetic flux into the receiver coil and the magnitude of the electrical current induced in the receiver coil are reduced.

FIG. 13A shows a flux generator base 248 in which drive shaft 232 rotates a ring permanent magnet 250 with a cylindrical tube 236' and permanent magnets 238, about the longitudinal axis of the drive shaft. A solenoid coil 252 is wound around drive shaft 232 and is coupled to an electrical current source/control 254. Electrical current provided by the electrical current source/control is varied to provide a controlled magnetic force that causes ring permanent magnet 250 to move downwardly along drive shaft 232 by a controlled amount. Mechanical links 256 are pivotally connected to the ring permanent magnet and extend through a slot 260 in the cylindrical tube to couple with pivot connections 258 on the facing poles of permanent magnets 238. As the ring permanent magnet is drawn down drive shaft 232, permanent magnets 238 are drawn radially inward toward each other, reducing the magnetic flux coupled into the receiver coil (not shown in this drawing) through flux linkage rods 240. Also, when the drive shaft is initially rotated, the permanent magnets are drawn relatively closer still to each other, thereby minimizing the startup torque by reducing the attraction between the permanent magnets and the flux linkage rods.

In FIG. 13B, an alternative flux generator base 262 is shown that achieves much the same result as flux generator base 248. However, in this embodiment, a swash plate 264 is connected to pivotal connectors 258 through mechanical links 256. Swash plate 264, cylindrical tube 236', and permanent magnets 238 are rotated by drive shaft 232. In this embodiment, bearing rollers 266 act on opposing surfaces of swash plate 264 to control its position along drive shaft 232 as the drive shaft rotates. The bearing rollers are mounted on a bracket 268 that is connected to a piston rod 270.

The position of the piston rod and thus, the position of the bearing rollers and swash plate, is adjusted by a pressurized fluid cylinder 272 that is actuated by applying pressurized hydraulic or pneumatic fluid through lines 274. The pressurized fluid is applied to drive the piston rod up or down and thereby move swash plate 264 up or down along drive shaft 232. As the swash plate moves down along drive shaft 232, it pulls permanent magnets 238 radially inward toward each other. In the fully retracted positions, permanent magnets are only weakly linked through flux linkage rods 240, and the startup torque necessary to begin rotating drive shaft 232 is minimal. As the swash plate is moved upwardly along drive shaft 232, the permanent magnets are forced outwardly, increasing the magnetic flux coupling between the rotating permanent magnets and the receiver coil. Accordingly, the magnitude of the electrical current induced in the receiver coil will be increased. It will be apparent that using either of the embodiments of the flux generator base shown in FIGS. 13A or 13B, the magnitude of the electrical current induced in the receiver coil is readily controlled.

FIG. 14 illustrates a flux generator base 280 that includes a housing 282 in which a divider 286 extends between an upper compartment 284 and an lower, generally dome-shaped, compartment 288 (as shown in the Figure). In upper compartment 284 are disposed a motor 290 that turns a drive shaft 292 at a relatively high speed, e.g., at more than 20,000 rpm. Mounted on drive shaft 292 is a rod-shaped permanent magnet 294. Motor 290 is energized with an electrical current controlled by a motor speed control circuit 296 that is disposed in lower compartment 288. The motor speed control circuit is generally conventional in design, including, for example, one or more silicon rectifiers or a triac, and is coupled to the motor through a lead 298. The motor speed control circuit is energized with electrical current supplied from a line current energized power supply 304 (or battery pack) to which the motor speed control circuit is connected. A speed control knob 306 extends above the housing of the flux generator base and is rotatable by the user to turn the device on or off and to vary the speed at which motor 290 rotates. Speed control knob 306 actuates a variable resistor 300, which is mounted just inside the top of the lower compartment, using a pair of threaded nuts 308. The variable resistor is connected to the motor speed control circuit through leads 302.

As illustrated in the Figure, flux generator base 280 is intended to be disposed so that permanent magnet 294 is generally adjacent to an air core receiver coil 276 (or other receiver coil). The term "air core" simply indicates that a ferrous alloy or other material having a relatively high magnetic permeability is not used as a core for this particular receiver coil. Instead, this embodiment of a receiver coil comprises a relatively flat or pancake-shaped coil wound of a conductor. Leads from the air core receiver coil supply electrical current to an appropriate conditioning circuit (not shown). An electrical current is induced to flow in the coil by the varying magnetic flux produced as permanent magnet 294 is rotated by the motor. Due to the speed at which permanent magnet 294 rotates, a relatively efficient magnetic flux coupling exists between the permanent magnet and the air core receiver coil.

By varying the speed at which the permanent magnet rotates, it is possible to control the magnitude of the current induced in the air core receiver coil. As the speed at which the permanent magnet rotates is increased, the magnitude of the electrical current produced by the air core receiver coil increases. It is contemplated that speed control knob 306 may be indexed to marks (not shown) that are provided on the exterior of housing 282 to indicate a range of electrical current for different settings of the speed control knob. Of course, the magnetic flux linkage can also be controlled by varying the separation between the flux generator base and the air core receiver coil.

Another embodiment of the present invention suitable for use in supplying energy to a portable device is shown in FIGS. 15A and 15B. The apparatus comprises two primary components, a flux generator base unit 310, and a receiving unit 312. The flux generator base unit comprises a housing 313, a pancake electric motor 314 rotating a shaft 316, and a rotor 318. As shown in FIG. 15B, preferably embedded in the rotor (or otherwise attached thereto) are a plurality of magnets 320. The magnets on one side of the rotor are oriented their north pole faces on the upper side of the rotor, while the magnets on the opposite side of the rotor have their south pole faces on the upper side of the rotor. In addition, the magnets are arranged in pairs such that each pair comprises an upwardly facing north pole on one side and an upwardly facing south pole on the opposite side and the magnets on each pair are disposed at different radiuses from the shaft. The rotor also may include a flux linkage bar 322, that operates in a manner similar to that of the flux linkage bars described above. It is preferable that the components comprising the flux generator be of low profile, so that the entire device is relatively wide and flat, so that the exterior shape of the base unit has the overall appearance of a "tablet."

The receiver unit may be either integrated into the portable device, or may comprise a separate component that is attached to the portable device. The receiver unit comprises a receiver coil 324, a wire coil 329, and a conditioning circuit 330 that is connected to the wire coil via leads 326. It is preferable that the receiver coil and wire coil be enclosed in a housing 311 (which may be the housing for the portable device). The conditioning circuit may also be included in the receiver unit housing, or may be separately disposed in the portable device. The receiver coil preferable comprises a magnetically permeable core sized so that the flux lines produced by the flux generator are optimally coupled with core when the receiver unit is properly aligned with the flux generator base unit. For example, opposing ends of the core comprising face portions 325 are disposed parallel to the poles of the magnets in the rotor of the flux generator base unit.

Wire coil 329 is wound around the core member so that when the variable magnetic field produced by the flux generator is inductively coupled into the receiver coil, a current is generated in the wire. This current is then rectified, filtered, and regulated by conditioning circuit 330, which provides a controlled output current at a suitable voltage for charging a battery 327 and/or energizing electronics 331 contained in the portable device. Conditioning circuits of this type are well known in the art, and may be purchased from various vendors as a single integrated circuit, such as a model MM1433 integrated circuit designed for charging a lithium ion battery made by the Mitsumi Corporation of Japan. It will be understood by those skilled in the art that a different conditioning circuit will be required for other types of batteries, e.g., a conditioning circuit specifically designed for use with nickel cadmium batteries will be required when the rechargeable battery is a nickel cadmium battery.

Three different size receiver coils 324 are shown in FIG. 15A to make clear that the flux generator base unit is universally usable with different size portable devices, but it should be clear that a receiver unit for a portable device would typically employ only one receiver coil. The use of three receiver coil core members and three sets of magnets shown in the Figure is purely for illustrative purposes. Also, a flux generator in the base unit may comprise only one pair of magnets. If a plurality of pairs of magnets are included, the magnets of different pairs can be disposed at circumferentially spaced-apart locations and not just diametrically opposite each other as shown in the Figure.

To save power and operational wear, it is desirable for the flux generator base unit to operate only when there is a load present (i.e., a battery to charge or electronics that are energized by the base unit. When a load is not present, the base unit should preferably be in a low power consuming "sleep" mode. Therefore, it will be necessary for the base unit to know when a load is present (so it can "wake up" and begin a charging or energy transfer operation) and to know when the battery is fully charged or the load is removed (so the base unit can turn off and go back to sleep). This behavior can be accomplished in a variety of ways. For example, a Hall-effect sensor 332 (or reed switch) is mounted in the flux generator unit and a magnet 334 is disposed in the center of the receiver unit so that the magnet is in close proximity to the Hall-effect sensor (or reed switch) when the receiver unit is placed on the flux generator base unit. The magnetic field produced by magnet 334 is sensed by the Hall-effect sensor (or reed switch), causing a change in the output of the sensor. (The change in the output signal of the sensor will depend on whether the sensor includes a normally-open or normally-closed switch condition). This sensor output signal is coupled through a lead 339 to a motor control 341 and enables the motor control to determine when a load is present so that it can wake up the base unit and energize the motor to produce a current in the receiver coil. In such circumstances, the motor will be with a current supplied through a lead 345 and the rotor will rotate, causing a variable magnetic field to be generated. Preferably, the Hall-effect sensor should be positioned in the center of the rotating magnetic field so that it is not significantly affected by it. Correspondingly, the receiver unit magnet should be disposed relative to the receiver and base units such that the receiver unit magnet and the Hall-effect sensor are in sufficiently close proximity to actuate the sensor only when the flux generator base unit and receiver unit are properly aligned and mated. It is preferable that when the Hall-effect sensor output changes state to indicate that the receiver unit has been properly positioned on the base unit, an indicator light 337 that is disposed in base unit will be energized with current supplied through a lead 343 by motor control 341. This same indicator light indicates that the base unit is in an operational mode (i.e., charging a battery). It is also contemplated that another indicator light 347 mounted on the receiver unit can be energized by the conditioning circuit when battery 327 in the receiver unit is fully charged, or conversely, the light can be extinguished when the battery is fully charged.

The conditioning circuit controls the current supplied for charging a battery and determines when the battery is fully charged. As discussed above, several vendors make suitable conditioning circuits for this purpose. When a battery charging cycle is complete, the energy consumed by the receiver unit from the flux generator base unit for battery charging will typically substantially decrease. This condition can be sensed in the flux generator by monitoring the current drawn by the electric motor. When the current is at a reduced level, the battery has either been fully charged or has been removed from the flux generator; in either case the flux generator motor can be turned off and go back to sleep.

In a more sophisticated feature of the apparatus, the receiver unit can communicate additional information (such as battery condition or status of the portable device, etc.) to the flux generator base unit for logging or display, by rapidly switching (i.e., pulsing) the current supplied by the conditioning circuit, thereby superimposing "digital" pulses relative to the load experienced by the electric motor in the flux generator base unit, causing corresponding pulses in the motor current due to the pulsed changes in the conditioning circuit load. The load on the motor will vary as a function of the energy being transferred to the receiver unit and consumed by the load, as controlled by the conditioning circuit. A rapid increase in load (even if only momentarily) can be "sensed" by a motor controller attempting to maintain a constant speed as a slowing of the rate at which the magnets are being rotated, which will require an increase in the motor current. Similarly, a rapid decrease in the load can be sensed by the motor controller, which must rapidly decrease the motor current to maintain a constant speed. The pulse fluctuation in the motor current due to the pulsing of the conditioning circuit load can thus be used to convey digital data between the receiver unit and the flux generator base unit. This pulse information evident in the motor current can then be decoded to interpret the data information provided from the receiver unit in the portable device, thereby effectively implementing a low-speed contactless communication channel from the portable device to the base unit. The information can be displayed at the base unit, or on a display (not shown) separate from the base unit. Optionally, the base unit could log the data passed to it from the portable device in an internal memory (not shown).

It is contemplated that the apparatus shown in FIGS. 15A and 15B could be adapted to be used with a variety of different-sized portable devices. For instance, by using a plurality of magnet pairs placed at different radii, various sized receiver units could be used with a single "universal" base unit. It is further contemplated that one of three or four standard sizes of receiver units might be employed in most portable devices or used as a separate component relative to the portable device.

As discussed above, it is also possible to generate a variable magnetic field by using motions other than a rotary motion. For example, as shown in a flux generator base unit 310' of FIG. 16, a linear motion could be applied to a pair of flux generator bars 336, each of which comprises a plurality of magnets 338 having north pole faces directed upwardly, and a plurality of magnets 340 with their south pole faces directed upwardly. As the flux generator bars are moved back and forth in a linear motion, a variable magnetic field is generated relative to a fixed magnetic receiver coil (not shown). The receiver coil can be of various sizes, so that its pole faces overlie different sets of permanent magnet poles. Although not shown, various well-known drive mechanisms could be used to provide the reciprocating linear motion driving the flux generator bars.

Another optional configuration comprising a flux generator base unit 310" is shown in FIG. 17, wherein a pair of flux generator bars 342 comprising magnets 344 are driven in elliptical path so that the pole faces of the magnets move relative to a fixed receiver coil (not shown), varying the magnetic flux in the receiver coil.

Further embodiments of universal base units and corresponding receiving units are shown in FIGS. 18A and 18B, and 19A and 19B. A primary feature of the universal base units shown in these Figures is the step configuration of housings 350 and 350'. (Note that elements having reference numbers with a prime notation in FIGS. 19A and 19B are substantially similar to the corresponding elements identified by same reference numbers—without a prime—in FIGS. 18A and 18B.) Preferably, the stepped housing is configured so that different sized receiver unit "tablets" 352, 354, and 356 can be easily mated with the base unit. Under this scheme, it is contemplated that the receiver unit tablets are either separate units, or integrated into the housing of the portable devices with which they are used. For example, the tablet portion of the receiving unit could be integrated into the bases of cylindrical battery modules having various predefined sizes. This design is an alternative to the various manufacturer-specific battery modules used in different power tool lines. In addition, the step configuration of the universal base units would be suitable for charging the batteries in portable devices having a cylindrical housing, such as electrically powered toothbrushes.

In order to obtain satisfactory performance using the step housing, it will be necessary for a rotor similar to rotor 358 to be used. Rotor 358 is generally cylindrical in shape, comprising a plurality of steps at diameters corresponding to the diameters of the steps in the housing. According to one embodiment, a plurality of arcuate magnets, similar to those discussed above with reference to FIG. 3H, are disposed in sets of opposite polar faces at various diameters, as shown in FIG. 18A. Optionally, wider, low-profile arcuate magnets 362 having opposite pole faces directed upwardly on opposite sides of the base unit could be employed, as shown in FIGS. 19A and 19B. As a further option, a plurality of cylindrical magnets 364 having opposite pole faces directed upwardly on opposite sides of the base unit can be used, as shown in FIG. 19A. Any of these options could be used to generate a varying magnetic flux as rotor 358 is rotated by pancake motor 314.

The receiver coil in the receiver unit must be sized to inductively couple with the flux generated by one of the sets of magnets used in the base unit. As was the case with the universal flux generator base unit of FIG. 15A, the use of three steps and three differently sized receiving units is purely illustrative. An actual device could employ either fewer or more steps and thus accept either correspondingly smaller or larger diameter receiving units.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A contactless energy transfer apparatus comprising:
    (a) portable receiving unit including:
        (i) a receiver coil: and
        (ii) a housing in which the receiver coil is disposed, said housing supporting the receiver coil: and
    a flux generator including:
        (i) a housing adapted to be disposed proximate to the housing of the receiving unit;
        (ii) a magnetic field generator comprising at least one permanent magnet disposed within the housing of the flux generator; and
        (iii) a prime mover drivingly coupled with the at least one permanent magnet, causing said at least one permanent magnet to move relative to the receiver coil, movement of said at least one permanent magnet producing a varying magnetic field that is coupled to the receiver coil, inducing an electrical current to flow in the receiver coil, wherein the prime mover is disposed outside the housing of the flux generator and is drivingly coupled with said at least one permanent magnet through a driven shaft.

2. A contactless energy transfer apparatus comprising:
    (a) portable receiving unit including:
        (i) a receiver coil; and
        (ii) a housing in which the receiver coil is disposed, said housing supporting the receiver coil; and
    (b) a flux generator including:
        (i) a housing adapted to be disposed proximate to the housing of the receiving unit;
        (ii) a magnetic field generator comprising a plurality of permanent magnets and a movable support on which the plurality of permanent magnets are mounted disposed within the housing of the flux generator; and
        (iii) a prime mover drivingly coupled to the movable support, causing said movable support to move relative to the receiver coil, movement of said movable support producing a varying magnetic field that is coupled to the receiver coil, inducing an electrical current to flow in the receiver coil, wherein the support is caused to move reciprocally back and forth in a reciprocating motion.

3. A contactless energy transfer apparatus comprising:
    (a) portable receiving unit including:
        (i) a receiver coil; and
        (ii) a housing in which the receiver coil is disposed, said housing supporting the receiver coil; and
    (b) a flux generator including:
        (i) a housing adapted to be disposed proximate to the housing of the receiving unit;
        (ii) a magnetic field generator comprising at least one permanent magnet disposed and a magnetic flux shunt disposed within the housing of the flux generator, the magnetic flux shunt being configured to be moveable between a shunt position, in which a magnetic field produced by said at least one permanent magnet of the magnetic field generator is shunted along a path that includes the receiver coil, and an unshunted position, in which a magnetic field produced by said at least one permanent magnet of the magnetic field generator is not shunted; and
        (iii) a prime mover drivingly coupled with the magnetic flux shunt, to cause the magnetic flux shunt to move between the shunt position and the unshunt position, thereby periodically shunting a magnetic field produced by said at least one permanent magnet of the magnetic field generator, causing the magnetic field to vary along a path that includes the receiver coil.

4. A contactless energy transfer apparatus comprising:
    (a) portable receiving unit including:
        (i) a receiver coil; and
        (ii) a housing in which the receiver coil is disposed, said housing supporting the receiver coil; and
    (b) a flux generator including:
        (i) a housing adapted to be disposed proximate to the housing of the receiving unit;
        (ii) a magnetic field generator comprising at least one permanent magnet disposed within the housing of the flux generator;
        (iii) a prime mover drivingly coupled with the at least one permanent magnet, causing said at least one permanent magnet to move relative to the receiver coil, movement of said at least one permanent magnet producing a varying magnetic field that is coupled to a core of the receiver coil, inducing an electrical current to flow in the receiver coil: and
        (iv) an adjustment member that is selectively actuatable to change a maximum magnetic flux that is coupled to the core of the receiver coil.

5. The energy transfer apparatus of claim 4, wherein the adjustment member controls a speed with which the element of the magnetic field generator is moved.

* * * * *

UNITED STATES PATENT AND TRADEMARK OFFICE
CERTIFICATE OF CORRECTION

PATENT NO. : 6,657,351 B2
DATED : December 2, 2003
INVENTOR(S) : Chen et al.

It is certified that error appears in the above-identified patent and that said Letters Patent is hereby corrected as shown below:

Column 9,
Line 24, "disk 62'" should read -- disk 62" --
Line 32, "FIG. 3F''" should read -- FIGURE 3F --
Line 33, "generator 60" should read -- generator 60'" --

Column 19,
Lines 22 and 43, after "(a)" insert -- a --
Line 26, before "a flux" insert -- (b) --

Column 20,
Lines 7 and 33, after "(a)" insert -- a --

Signed and Sealed this

Twenty-fifth Day of January, 2005

JON W. DUDAS
*Director of the United States Patent and Trademark Office*